United States Patent [19]

Whitten

[11] Patent Number: 5,194,430

[45] Date of Patent: Mar. 16, 1993

[54] HETEROCYCLIC-NMDA ANTAGONISTS

[75] Inventor: Jeffrey P. Whitten, Cincinnati, Ohio

[73] Assignee: Merrell Dow Pharmaceuticals Inc., Cincinnati, Ohio

[21] Appl. No.: 675,156

[22] Filed: Mar. 28, 1991

Related U.S. Application Data

[63] Continuation-in-part of Ser. No. 525,290, May 17, 1990, abandoned.

[51] Int. Cl.⁵ .................. C07F 9/06; A61K 31/675
[52] U.S. Cl. ................................. 514/89; 546/22
[58] Field of Search ................. 514/89; 546/22, 227, 546/228

[56] References Cited

U.S. PATENT DOCUMENTS

| | | | |
|---|---|---|---|
| 2,706,194 | 4/1955 | Morris | 546/22 X |
| 3,361,784 | 1/1968 | Leu | 546/22 X |
| 4,132,542 | 1/1979 | Aya et al. | 71/86 |
| 4,657,899 | 4/1987 | Rzeszotarski et al. | 514/120 |
| 4,746,653 | 5/1988 | Hutchison et al. | 514/89 |

FOREIGN PATENT DOCUMENTS

| | | |
|---|---|---|
| 0159889 | 1/1990 | European Pat. Off. |
| 0203891 | 1/1990 | European Pat. Off. |
| 9208724 | 5/1992 | PCT Int'l Appl. |

Primary Examiner—Marianne M. Cintins
Assistant Examiner—Catherine S. Kilby Scalzo
Attorney, Agent, or Firm—J. Michael Dixon

[57] ABSTRACT

The present invention is directed to a class of 3-phosphono-piperidine and pyrrolidine derivatives and their use as NMDA antagonists.

46 Claims, No Drawings

HETEROCYCLIC-NMDA ANTAGONISTS

This is a continuation-in-part of Ser. No. 525,290, filed on May 17, 1990 now abandoned.

The present invention is directed to a class of 3-[functionalized alkylphosphono]-piperidine and pyrrolidine compounds that are useful as NMDA antagonists. Another aspect of the invention is directed to the use of these compounds in the treatment of a number of disease states. A further aspect of this invention is directed to pharmaceutical compositions containing these compounds.

In accordance with the present invention a new class of NMDA antagonists have been discovered which can be described by the following formula:

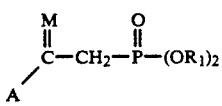

Formula I in which $R_1$ is represented by hydrogen, $C_{1-4}$ alkyl or $CF_3$; M is represented by O, N-O-$R_4$ or

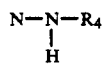

in which $R_4$ is represented by hydrogen, $C_{1-4}$ alkyl or phenylalkyl;

A is represented by one of the following substituents:

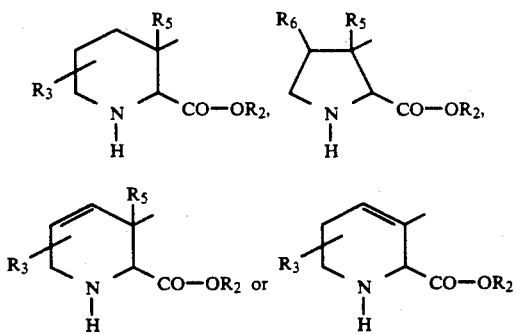

$R_2$ is represented by hydrogen, $C_1-C_4$ alkyl, cycloalkyl, trialkylamino, phenylalkyl, phenyl, substituted phenyl, or trifluoromethyl; $R_3$ is represented by hydrogen, $C_1-C_4$ alkyl, phenyl, phenylalkyl, or cyclohexylmethyl; $R_5$ is represented by hydrogen, linear $C_1-C_4$ alkyl, or phenylalkyl; $R_6$ is represented by hydrogen, $C_1-C_4$ alkyl, phenyl, phenylalkyl, or cyclohexylmethyl; or a pharmaceutically acceptable salt thereof. As used in this application:

a) the terms "lower alkyl group and $C_1-C_4$ alkyl" refer to a branched or straight chained alkyl group containing from 1-4 carbon atoms, such as methyl, ethyl, n-propyl, isopropyl, n-butyl, isobutyl, etc;

b) the terms "lower alkoxy group and $C_1-C_4$ alkoxy" refer to a straight or branched alkoxy group containing from 1-4 carbon atoms, such as methoxy, ethoxy, n-propoxy, isopropoxy, n-butoxy, isobutoxy, etc.;

c) the term "cycloalkyl" refers to a cyclohexyl or a cyclopentyl group;

d) the term "substituted phenyl ring" refers to a phenyl ($C_6H_5$) which is substituted with up to 3 substituents, each substituent is independently selected from the group consisting of halogens, $C_1-C_4$ alkyl, $C_1-C_4$ alkoxy, $CF_3$, $OCF_3$, OH, CN, $COOR_6$, and $CONR_6R_7$ in which $R_6$ and $R_7$ are represented by hydrogen or a $C_1-C_4$ alkyl. These substituents may be the same or different and may be located at any of the ortho, meta, or para positions;

e) the term "phenylalkyl substituent" refers to the following structure —$(CH_2)_m$—$C_6H_5$, in which m is an integer from 1-3. This phenyl ring may be substituted in the manner described immediately above;

f) the term "oxime" refers to compounds in which M is represented by N—O—$R_4$;

g) the term "hydrazone" refers to compound in which M is represented by, N—NH—$R_4$;

h) the term "pharmaceutically acceptable addition salt" refers to either a pharmaceutically acceptable acid addition salt or a pharmaceutically acceptable basic addition salt;

i) the term "halogen" refers to a fluorine or chlorine atom;

j) the term "trialkylamino" refers to

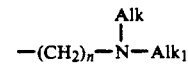

in which n is represented by an integer from 2-4 and Alk and $Alk_1$ are each independently represented by a $C_1-C_4$ alkyl; and k) the term "cyclohexylmethyl" refers to —$CH_2$—$C_6H_{12}$.

The expression "pharmaceutically acceptable acid addition salts" is intended to apply to any non-toxic organic or inorganic acid addition salt of the base compounds represented by Formula I, or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by Formula I, or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

All of the compounds of Formula I contain at least two (2) asymmetric centers and thus will exist as diasteriosmers. Any reference to these compounds as well as their intermediates should be construed as encompassing a racemic mixture, a specific optical isomer or a pair of enantiomers. The specific optical isomers can be synthesized as shown herein or can be recovered by techniques known in the art such as chromatography on chiral stationary phases, or resolution via chiral salt formation and subsequent separation by selective crystallization. HPLC ion exchange chromatography may be utilized to separate only the diastereomers.

Examination of Formula I shows that some of the compounds contain a carbonyl function in the alkyl chain which is bonded to the 3-position of the piperidinyl ring or the pyrrolidinyl ring. These compounds will exist in a state of tautomeric equilibrium in which the carbonyl function will participate in a keto-enol equilibrium reaction. This tautomerism may be depicted as follows:

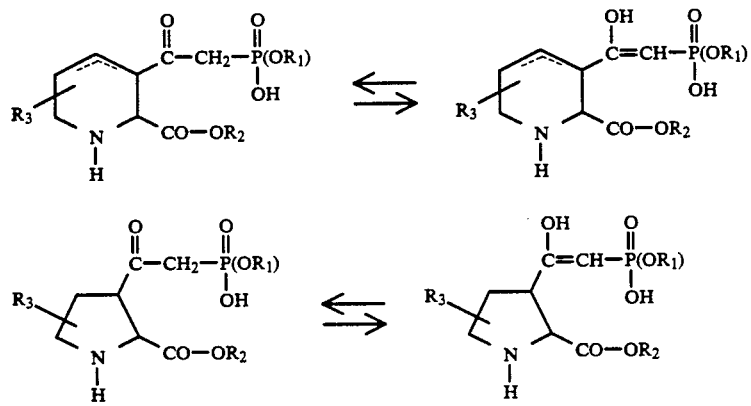

As is readily apparent to those skilled in the art, the enol form of this molecule will also exist as geometrical isomers and thus can exist in either the cis or trans orientation.

As is indicated by the $R_3$ substituent, the piperidine ring may be further substituted at positions 4, 5, or 6. $R_3$ may optionally represent up to 2 non-hydrogen substituents. Only one non-hydrogen substituent should be located at any one position on the piperidine ring. If two non-hydrogen substituents are present, they may be the same or different. When $R_3$ is a non-hydrogen substituent, then this substituent may be either syn or anti relative to the phosphono substituent.

As is indicated by the dotted line in the piperidinyl structure, a double bond may exist at positions 3 or 4.

Illustrative examples of compounds encompassed by Formula I include:
3-(Phosphonoacetyl)piperidine-2-carboxylic acid;
3-(Phosphonoacetyl)piperidine-4-methyl-2-carboxylic acid;
3-[1-[(Phenylmethoxy)imino]-2-phosphonoethyl]piperidine-2-carboxylic acid;
3-(Phosphonoacetyl)piperidine-5-methyl-2-carboxylic acid;
3-[(1-Methoxyimino)-2-phosphonoethyl]piperidine-5-methyl-2-carboxylic acid;
3-(Phosphonoacetyl)piperidine-2-carboxylic acid, ethyl ester;
3-(Phosphonoacetyl)piperidine-5-(1-phenylmethyl)-2-carboxylic acid;
3-(Phosphonoacetyl)piperidine-4,5-dimethyl-2-carboxylic acid;
3-(Phosphonoacetyl)piperidine-5-propyl-2-carboxylic acid;
3-[1-[(Phenylmethoxy)imino]-5-propyl-2-phosphonoethyl]piperidine-2-carboxylic acid;
3-(Phosphonoacetyl)piperidine-5-methyl-2-carboxylic acid, ethyl ester;
3-(Phosphonoacetyl)piperidine-5-propyl-2-carboxylic acid, ethyl ester;
d,l-trans-3-(Phosphonoacetyl)piperidine-2-carboxylic acid;
d,l,cis-3-(Phosphonoacetyl)piperidine-2-carboxylic acid
3(S)-[(Diethoxyphosphinyl)acetyl]piperidine-2(R)-carboxylic acid, methyl ester;
3(S)-[(Diethoxyphosphinyl)acetyl]piperidine-4-methyl-2(R)-carboxylic acid, methyl ester;
3(R)-[(Diethoxyphosphinyl)acetyl]piperidine-4-methyl-2(S)-carboxylic acid, methyl ester;
3(S)-(Phosphonoacetyl]piperidine-4-methyl-2(R)-carboxylic acid;
3(R)-(Phosphonoacetyl]piperidine-4-methyl-2(S)-carboxylic acid;
3(S)-[(Diethoxyphosphinyl)acetyl]piperidine-5-methyl-2(R)-carboxylic acid, methyl ester;
3(S)-(Phosphonoacetyl]piperidine-5-methyl-2(R)-carboxylic acid;
d,l,cis-3-[(Diethoxyphosphinyl)acetyl]piperidine-2-carboxylic acid, methyl ester;
3(S)-(Phosphonoacetyl]piperidine-2(R)-carboxylic acid;
3(S)-(Phosphonoacetyl]piperidine-5-methyl-2(R)-carboxylic acid;
3(S)-(Phosphonoacetyl]piperidine-5-benzyl-2(R)-carboxylic acid;
3(S)-(Phosphonoacetyl]piperidine-3(R)-methyl-2(R)-carboxylic acid;
3(S)-(Phosphonoacetyl]piperidine-5-benzyl-3(R)-methyl-2(R)-carboxylic acid;
3-(Phosphonoacetyl]-3-piperidene-2(R)-carboxylic acid;
3-(Phosphonoacetyl]-3-piperidene-5-methyl-2(R)-carboxylic acid;
3(S)-(Phosphonoacetyl]-4-piperidene-2(R)-carboxylic acid;
3(S)-(Phosphonoacetyl]-3(R)-methyl-4-piperidene-2(R)-carboxylic acid;
3(S)-(Phosphonoacetyl]-3(R)-methyl-5-methyl-4-piperidene-2(R)-carboxylic acid;

3(S)-(Phosphonoacetyl]-3(R)-methyl-5-benzyl-4-piperi-
dene-2(R)-carboxylic acid;
d,l-cis-3-(Phosphonoacetyl]pyrrolidine-4-methyl-2-car-
boxylic acid;
d,l,trans-3-(Phosphonoacetyl]pyrrolidine-4-methyl-2-
carboxylic acid
d,l-cis-3-(Phosphonoacetyl]pyrrolidine-2-carboxylic
acid;
d,l,trans-3-(Phosphonoacetyl]pyrrolidine-2-carboxylic
acid
d,l,cis-3-(Phosphonoacetyl]pyrrolidine-3-methyl-2-car-
boxylic acid;

d,l-trans-3-(Phosphonoacetyl]pyrrolidine-3-methyl-2-
carboxylic acid.

It is preferred for A to be a saturated piperidine ring and for M to be O. $R_3$ and $R_5$ are preferably hydrogen. The preferred stereo-chemistry is 2R, 3S.

The saturated piperidine compounds of Formula I in which M is represented by O and $R_5$ is represented by hydrogen, can be prepared utilizing techniques known in the art. One method for preparing these compounds is illustrated below in Reaction Scheme A. In Scheme A, all substituents are as previously defined unless otherwise indicated.

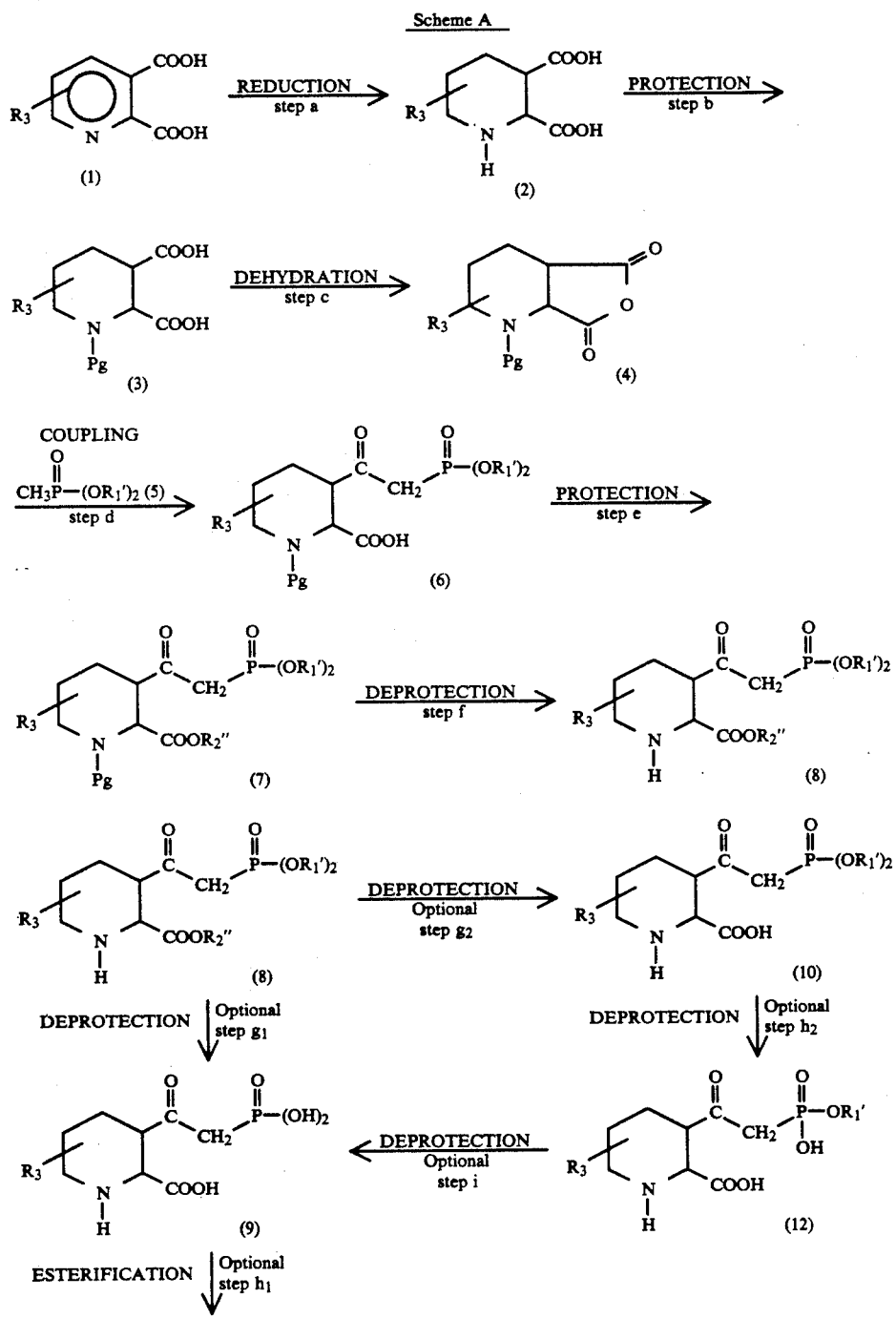

Scheme A

-continued

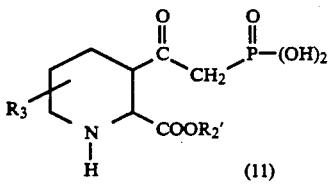

Ph = Protecting group
R₁' = C₁-C₄ alkyl or CF₃R₂' = C₁-C₄ alkyl, cycloalkyl, trialkylamino, alkylphenyl, phenyl, substituted phenyl, or trifluoromethylR₂'' = CH₂C₆H₅ or C₁-C₄ alkyl Scheme A provides a general synthetic procedure for preparing the saturated piperidine compounds of Formula I in which M is represented by O and $R_5$ is represented by hydrogen.

In step a, the appropriate pyridine-2,3-dicarboxylic acid derivative of structure (1) is reduced to give the corresponding piperidine-2,3-dicarboxylic acid derivative of structure (2) using techniques and procedures well known in the art.

For example, the appropriate pyridine-2,3-dicarboxylic acid derivative of structure (1) is contacted with an appropriate reducing agent, such as nickel/aluminum, palladium, or platinum in the presence of hydrogen, nickel/aluminum being preferred. The reactants are typically contacted in aqueous base such as sodium hydroxide. The reactants are typically stirred together for a period of time ranging from 6 hours to 5 days and at a temperature range of from 20°-38° C. The piperidine-2,3-dicarboxylic acid derivative of structure (2) is recovered from the reaction zone by removing the catalyst by filtration. It may be used in solution without isolation or recovered by extraction and purification by chromatography.

In step b, the appropriate piperidine-2,3-dicarboxylic acid derivative of structure (2) is protected to give the corresponding N-protected-piperidine-2,3-dicarboxylic acid derivative of structure (3). A variety of protecting groups may be utilized such as, for example, benzyloxycarbonyl (CBZ). Other suitable protecting groups include substituted carbamates such as t-butyloxycarbonyl and phenylfluorenyl (PhF).

These protecting groups may be placed on the nitrogen atom by techniques known in the art. If the protecting group is CBZ, for example, the appropriate piperidine-2,3-dicarboxylic acid derivative of structure (2) is contacted with a molar excess of benzyl chloroformate or [2-(tertbutoxycarbonyloxyimino)-2-phenylacetonitrile] or 9-phenylfluorenyl bromide. The reactants are typically contacted in a suitable organic solvent such as aqueous dioxane. The reactants are typically stirred together at room temperature for a period of time ranging from 2-24 hours. The N-protected-piperidine-2,3-dicarboxylic acid derivative of structure (3) is recovered from the reaction zone by extractive methods as is known in the art. It may be purified by recrystallization.

Alternatively, if the protecting group is N-(9-phenylfluorenyl), for example, the appropriate piperidine-2,3-dicarboxylic acid derivative of structure (2) is contacted with a molar excess of 9-phenylfluorenyl bromide, a molar excess of a suitable base such as diisopropylethylamine and a molar deficiency of lead nitrate. The reactants are typically contacted in a suitable organic solvent such as acetonitrile. The reactants are typically stirred together at room temperature for a period of time ranging from 2-24 hours. The N-(9-phenylfluorenyl)piperidine-2,3-dicarboxylic acid derivative of structure (3) is recovered from the reaction zone by extractive methods as is known in the art. It may be purified by silica gel chromatography.

In step c, the 2,3-dicarboxylic acid functionality of the appropriate N-protected-piperidine-2,3-dicarboxylic acid derivative of structure (3) is dehydrated to give the corresponding N-protected-piperidino anhydride derivative of structure (4).

For example, the N-protected-piperidine-2,3-dicarboxylic acid derivative of structure (3) is contacted with a molar excess of acetic anhydride. The reactants are typically stirred together for a period of time ranging from 2-3 days at temperature range of from 20°-100° C. under an inert atmosphere such as nitrogen. The N-protected-piperidino anhydride derivative of structure (4) is recovered from the reaction zone by evaporation of the solvent.

In step d, the appropriate N-protected-piperidino anhydride derivative of structure (4) is coupled with the appropriate phosphonate ester of structure (5) to give the corresponding N-protected-3-[(dialkoxyphosphinyl)acetyl]piperidine-2-carboxylic acid of structure (6). The appropriate phosphonate ester of structure (5) is one in which $R_1$ is represented by a $C_1$-$C_4$ alkyl or a trifluoromethyl group. These alkyl functionalities serve to act as protecting groups during the coupling reactions. One of these $R_1$ functions will be cleaved during the deprotection reaction of optional step h₂ which is described below and the second may also be hydrolysed if desired as described in optional step i which is described below. Alternatively, both protecting groups may be hydrolysed in one step as described in optional step g₁ which is described below. As is obvious to those skilled in the art, the particular protecting group utilized should correspond to that desired in the final product if $R_1$ is not to be represented by hydrogen in the final product.

For example, the appropriate phosphonate ester of structure (5) is first contacted with a molar equivalent of an appropriate strongly basic reagent such as n-butyllithium. The reactants are typically contacted in a suitable organic solvent such as tetrahydrofuran under an inert atmosphere such as nitrogen. The reactants are typically stirred together for a period of time ranging from 10-20 minutes and at a temperature of −78° C. At that point the reaction medium is warmed to about −10° C. and a molar equivalent of the appropriate N-protected-piperidino anhydride derivative of structure (4) is then added. The reactants are typically stirred together for a period of time ranging from 1-3 hours at a temperature range of from −78° C. to −20° C. The N-protected-3-[(dialkoxyphosphinyl)acetyl]piperidine-2-carboxylic acid of structure (6) is recovered from the reaction zone by extractive methods as is known in the art. It may be purified by chromatography.

In step e, the 2-carboxylic acid functionality of the appropriate N-protected-3-[(dialkoxyphosphinyl)acetyl]piperidine-2-carboxylic acid of structure (6) is protected as its benzyl or $C_1$–$C_4$ alkyl ester to give the corresponding N-protected-3-[(dialkoxyphosphinyl)acetyl]piperidine-2-carboxylic acid, benzyl or $C_1$–$C_4$ alkyl ester of structure (7). These protecting groups can be placed on the molecule using techniques known in the art.

For example, the appropriate N-protected-3-[(dialkoxyphosphinyl)acetyl]piperidine-2-carboxylic acid of structure (6) is contacted with a molar excess of an alkyl bromide of the formula $R_2''Br$, wherein $R_2''$ is represented by benzyl or $C_1$–$C_4$ alkyl, and a molar excess of an appropriate non-nucleophilic base such as dicyclohexyl amine. The reactants are typically contacted in a suitable aprotic solvent such as dimethylformamide in an inert atmosphere such as nitrogen. The reactants are typically stirred together for a period of time ranging from 1–4 hours and at a temperature range of from 20° to 65° C. The N-protected-3-[(dialkoxyphosphinyl)acetyl]piperidine-2-carboxylic acid, benzyl or $C_1$–$C_4$ alkyl ester of structure (7) is recovered from the reaction zone by extractive methods as is known in the art. It may be purified by chromatography.

In step f, the N-protecting group of the appropriate N-protected-3-[(dialkoxyphosphinyl)acetyl]piperidine-2-carboxylic acid, benzyl or $C_1$–$C_4$ alkyl ester of structure (7) is removed to give the corresponding 3-[(dialkoxyphosphinyl)acetyl]piperidine-2-carboxylic acid, benzyl or $C_1$–$C_4$ alkyl ester of structure (8).

For example, the appropriate N-protected-3-[(dialkoxyphosphinyl)acetyl]piperidine-2-carboxylic acid, benzyl or $C_1$–$C_4$ alkyl ester of structure (7) is contacted with a molar excess of an appropriate such as aqueous hydrochloric acid, trifluoroacetic acid or a mixture of hydrochloric acid in dioxane. The reactants are typically stirred together at room temperature for a period of time ranging from 1–5 hours. The 3-[(dialkoxyphosphinyl)acetyl]piperidine-2-carboxylic acid, benzyl or $C_1$–$C_4$ alkyl ester of structure (8) is recovered from the reaction zone by neutralization with propylene oxide followed by filtration or by chromatography.

In optional step $g_1$, the 2-carboxylic acid ester and both of the phosphonate ester functionalities of the appropriate 3-[(dialkoxyphosphinyl)acetyl]piperidine-2-carboxylic acid, benzyl or $C_1$–$C_4$ alkyl ester of structure (8) are removed to give the 3-(phosphonoacetyl)piperidine-2-carboxylic acid of structure (9).

For example, the appropriate 3-[(dialkoxyphosphinyl)acetyl]piperidine-2-carboxylic acid, benzyl or $C_1$–$C_4$ alkyl ester of structure (8) is typically contacted with a 3 to 6 molar solution of hydrochloric acid. The reactants are typically stirred together at a temperature range of from room temperature to reflux for a period of time ranging from 1 to 30 hours. The 3-(phosphonoacetyl)piperidine-2-carboxylic acid of structure (9) is recovered from the reaction medium by techniques known in the art such as precipitation as its free base with propylene oxide. It may then be purifed by recrystallization from a solvent system such as, for example, ethanol/isopropanol.

In optional step $g_2$, the 2-carboxylic acid ester functionality of the appropriate 3-[(dialkoxyphosphinyl)acetyl]piperidine-2-carboxylic acid, benzyl or $C_1$–$C_4$ alkyl ester of structure (8) is removed to give the 3-[(dialkoxyphosphinyl)acetyl]piperidine-2-carboxylic acid of structure (10).

For example, appropriate 3-[(dialkoxyphosphinyl)acetyl]piperidine-2-carboxylic acid, benzyl or $C_1$–$C_4$ alkyl ester of structure (8) is typically contacted with a 1 to 3 molar solution of hydrochloric acid. The reactants are typically stirred together at a temperature range of from room temperature to reflux for a period of time ranging from 1 to 18 hours. The 3-[(dialkoxyphosphinyl)acetyl]piperidine-2-carboxylic acid of structure (10) is recovered from the reaction medium by techniques known in the art such as such as precipitation as its free base with propylene oxide. It may then be purifed by recrystallization from a solvent system such as, for example, ethanol/isopropanol.

In optional step $h_1$, the 2-carboxylic acid functionality of the appropriate 3-(phosphonoacetyl)piperidine-2-carboxylic acid of structure (9) is reesterified to give the 3-(phosphonoacetyl)piperidine-2-carboxylic acid, ester of structure (11).

For example, the appropriate 3-(phosphonoacetyl)piperidine-2-carboxylic acid of structure (9) is contacted with an acidic solution of the desired alcohol. The reactants are typically refluxed for a period of time ranging from 2–24 hours. The 3-(phosphonoacetyl)piperidine-2-carboxylic acid, ester of structure (11) is recovered from the reaction zone by extractive methods as is known in the art. It may be purified by chromatography.

Alternatively, the appropriate 3-(phosphonoacetyl)piperidine-2-carboxylic acid of structure (9) can be contacted with a compound of the formula $R_2Br$ in which $R_2$ represents the desired $R_2$ substituent. The reactants are typically contacted in dimethyl formamide in the presence of a base such as dicyclohexylamine. The 3-(phosphonoacetyl)piperidine-2-carboxylic acid, ester of structure (11) is recovered from the reaction zone by extractive methods as is known in the art. It may be purifed by chromatography. Other suitable esterification methods may also be utilized.

One of the protecting groups of the phosphonate ester, represented by $R_1'$, is removed and depending upon the manner in which the deprotection reaction is carried out, the other protecting group represented by $R_1'$ may also be removed.

In optional step $h_2$, one of the phosphonate ester functionalites of the appropriate 3-[(dialkoxyphosphinyl)acetyl]piperidine-2-carboxylic acid of structure (10) is hydrolyzed to give the corresponding 3-[(monoalkoxyphosphinyl)acetyl]piperidine-2-carboxylic acid of structure (12).

For example, appropriate 3-[(dialkoxyphosphinyl)acetyl]piperidine-2-carboxylic acid of structure (10) is typically contacted with a 2 to 5 molar solution of hydrochloric acid. The reactants are typically stirred together at a temperature range of from room temperature to reflux for a period of time ranging from 1 to 18 hours. The 3-[(monoalkoxyphosphinyl)acetyl]piperidine-2-carboxylic acid of structure (12) is recovered from the reaction medium by techniques known in the art such as precipitation as its free base with propylene oxide. It may then be purifed by recrystallization from a solvent system such as, for example, ethanol/isopropanol.

In optional step i, the remaining phosphonate ester functionality of the appropriate 3-[(monoalkoxyphosphinyl)acetyl]piperidine-2-carboxylic acid of structure

(12) is hydrolyzed to give the 3-(phosphonoacetyl)-piperidine-2-carboxylic acid of structure (9).

For example, appropriate 3-[(monoalkoxyphosphinyl)acetyl]piperidine-2-carboxylic acid of structure (12) is typically contacted with a 3 to 6 molar solution of hydrochloric acid. The reactants are typically stirred together at a temperature range of from 60° C. to reflux for a period of time ranging from 1 to 30 hours. The 3-(phosphonoacetyl)piperidine-2-carboxylic acid of structure (9) is recovered from the reaction medium by techniques known in the art such as such as precipitation as its free base with propylene oxide. It may then be purifed by recrystallization from a solvent system such as, for example, ethanol/isopropanol.

Alternatively, all 4 protecting groups (i.e. Pg, $R_2''$, and both $R_1'$ functionalities) can be removed by combining step f and step $g_1$ and subjecting the N-protected-3-[(dialkoxyphosphinyl)acetyl]piperidine-2-carboxylic acid, benzyl or $C_1$-$C_4$ alkyl ester Of structure (7) to a vigorous acidic hydrolysis. This can be accomplished by contacting the appropriate N-protected-3-[(dialkoxyphosphinyl)acetyl]piperidine-2-carboxylic acid, benzyl or $C_1$-$C_4$ alkyl ester of structure (7) with a 6 molar solution of a mineral acid such as HCL for a period of time ranging from 18 to 24 hours at a temperature range of from room temperature to reflux. The 3-(phosphonoacetyl)piperidine-2-carboxylic acid of structure (9) can be recovered from the reaction zone by techniques known in the art such as such as precipitation as its free base with propylene oxide. It may then be purified by recrystallization from a solvent system such as, for example, ethanol/isopropanol.

Also, where the 2-carboxylic acid ester functionality of the appropriate 3-[(dialkoxyphosphinyl)acetyl]-piperidine-2-carboxylic acid, benzyl or $C_1$-$C_4$ alkyl ester of structure (8) is benzyl or t-butyl, both of the phosphonate ester functionalities may be removed to give the 3-(phosphonoacetyl)piperidine-2-carboxylic acid, benzyl or t-butyl ester of structure (11).

For example, the appropriate 3-[(dialkoxyphosphinyl)acetyl]piperidine-2-carboxylic acid, benzyl or t-butyl ester of structure (8) is contacted with a molar excess of trimethylsilylbromide or trimethylsilyliodide. The reactants are typically contacted in a suitable organic solvent such as methylene chloride or acetonitrile. The reactants are typically stirred together at room temperature for a period of time ranging from 4–24 hours. The 3-(phosphonoacetyl)piperidine-2-carboxylic acid, benzyl or t-butyl ester of structure (11) is recovered from the reaction zone by techniques known in the art such as such as precipitation as its free base with propylene oxide. It may then be purified by recrystallization from a solvent system such as, for example, ethanol/isopropanol.

The proper starting material for the reduction of step a is a pyridine-2,3-dicarboxylic acid derivative of structure (1), in which $R_3$ is represented by the same substituent as is desired in the final product. Starting materials for use in Scheme A are readily available to one of ordinary skill in the art. For example, certain pyridine-2,3-dicarboxylic acid derivatives are described in J. Med. Chem. 10, 1065 1974 and certain phosphonate esters of structure (5) are described in Tetrahedron Letters 22 2829-31 1976.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "mp" refers to melting point; "°C." refers to degrees Celsius; "mm Hg" refers to millimeters of mercury; "μL" refers to microliters; "μg" refers to micrograms; and "μM" refers to micromolar.

EXAMPLE 1

3-(Phosphonoacetyl)piperidine-2-carboxylic acid

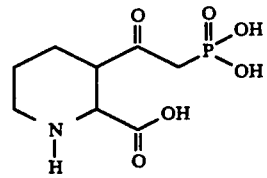

Step a: Piperidine-2,3-dicarboxylic acid

Dissolve pyridine-2,3-dicarboxylic acid (20 g, 120 mmol) in 0.5N aqueous sodium hydroxide (900 mL). Add nickel/aluminum powder (45 g) in portions over 3 hours. Stir for 4 days, filter off the catalyst to yield the title compound in clear solution. The resulting free amine is not isolated.

Step b: N-Carbobenzoxypiperidine-2,3-dicarboxylic acid

Add benzyl chloroformate (20 mL, 167 mmol) to the above solution of piperidine-2,3-dicarboxylic acid (120 mmol) along with dioxane (200 mL). Stir overnight and acidify to a pH of 1 with 6N hydrochloric acid. Extract with methylene chloride (400 mL) followed by ethyl acetate (200 mL). Combine the organic phases and dry (MgSO$_4$). Evaporate the solvent in vacuo to give a clear oil (35.9 g, 98%). Recrystallize (chloroform) to give the title compound as a white solid as predominantly the trans D,L compounds (10.9 g). Evaporate the residue to give the title compound as a white semi-solid as approprimately a 2:1 cis/trans mixture of diastereomers.

$^1$H NMR (300 MHz, d$_6$DMSO) ppm 12.9 (bs), 7.35 (m), 5.2 (m), 4.5 (s), 3.9 (d), 2.6 (s), 3.4 (m), 3.15 (s), 3.1 (m), 2.8 (m), 2.6 (m), 2.1 (m), 1.9 (m), 1.6 (m), 1.45 (m).

Step c: N-Carbobenzoxypiperidine-2,3-dicarboxylic acid anhydride

Dissolve the 2:1 cis/trans mixture of N-carbobenzoxypiperidine-2,3-dicarboxylic acid diastereomers (20 g) in acetic anhydride (500 mL) and stir overnight under a dry nitrogen atmosphere. Vacuum distill off the acetic anhydride to leave the title compound as a red glass (11.1 g, 59%).

$^1$H NMR (90 MHz, CDCl$_3$) ppm 7.3 (s), 5.4 (m), 5.2 (s), 4.0 (m), 3.1 (m), 2.9 (m), 2.2 (m). 1.7 (m).

Step d: N-Carbobenzoxy-3[(diethoxyphosphinyl)acetyl]-piperidine-2-carboxylic acid Dissolve methyl diethyl phosphonate (5.5 g, 36.4 mmol) in anhydrous tetrahydrofuran (150 mL) and place under a dry nitrogen atmosphere. Cool to −78° C. and add n-butyllithium (14.0 mL of a 2.6M solution, 36.4 mmol). Stir for 10 minutes and quickly add a pre-cooled −60° C. solution of N-carbobenzoxypiperidine- 2,3-dicarboxylic acid anhydride (11 g, 3.8 mmol) in anhydrous tetrahydrofuran (150 mL). Stir for 2 hours at −78° C. and allow to warm to −20° C. over 1½ hours. Pour the reaction mixture into 1.0N hydrochloric acid (1½ L) and extract with methylene chloride (2×500 mL). Combine the organic phases, dry (MgSO₄) and evaporate the solvent in vacuo to give the title compound.

Step e:
N-Carbobenzoxy-3[(diethoxyphosphinyl)acetyl]-piperidine-2-carboxylic acid, benzyl ester Dissolve N-carbobenzoxy-3[(diethoxyphosphinyl)acetyl]-piperidine-2-carboxylic acid (36.4 mmol) in dimethylformamide (200 mL) and place under a nitrogen atmosphere. Add benzyl bromide (10.5 mL, 81 mmol) and dicyclohexyl amine (16.2 mL, 89 mmol) and heat to 65° C. Allow to cool slowly to room temperature and filter. Pour the filtrate into water (1½ L) and extract with ethyl acetate (2×500 mL). Combine the organic phases and dry (MgSO₄). Evaporate the solvent in vacuo to give a brown oil. Purify by flash chromatography (ethyl acetate) to give the title compound as a yellow oil (3.6 g, 19%).

Step f: 3-(Phosphonoacetyl)piperidine-2-carboxylic acid

Mix N-carbobenzoxy-3[(diethoxyphosphinyl)acetyl]-piperidine-2-carboxylic acid benzyl ester (3.6 g) and 6N hydrochloric acid (400 mL) and reflux for 24 hours. Condense with a stream of nitrogen and dissolve the residue in a mixture of absolute ethanol (75 mL) and isopropanol (75 mL). Filter and add propylene oxide until a white precipitate develops. Filter the precipitate, wash with isopropanol and dry to give the title compound as a white powder (1.55 g, 91%).

MS (FAB/glycerol) 252(M+H);

¹H NMR (3000 mHz, D₂O) ppm 4.6 (m), 4.4 (m), 4.3 (m), 4.15 (d), 4.05 (d), 3.85 (m), 3.75 (d), 3.7 (d), 3.65 (q), 3.45 (m), 3.4 (m), 3.1 (m), 3.05 (d), 3.0 (d), 2.85 (d), 2.45 (m) 2.4 (m), 2.2 (m), 2.1 (m), 2.05 (m), 1.95 (m), 1.85 (m), 1.8 (m), 1.75 (m), 1.6 (m), 1.55 (m), 1.45 (m), 1.2 (d), 1.115 (t).

¹³C NMR ppm 212.0, 211.9, 211.7, 171.1, 173.8, 60.3, 60.2, 59.3, 59.2, 50.7, 50.0, 46.7, 45.8, 27.2, 26.4, 25.8, 22.6, 21.0, 19.5.

³¹P NMR (decoupled) ppm 12.56 and 12.42.

Anal. Calcd for $C_8H_{14}NO_6P \cdot 1.5H_2O$: C, 34.54, H, 6.07; N, 5.11; Found: C, 34.76; H, 5.58; N, 4.69.

The saturated piperidine compounds of Formula I in which M is represented by O and R₅ is represented by hydrogen can be separated into their diastereomeric pairs as shown in Scheme B. In Scheme B, all substituents unless otherwise indicated are as previously defined.

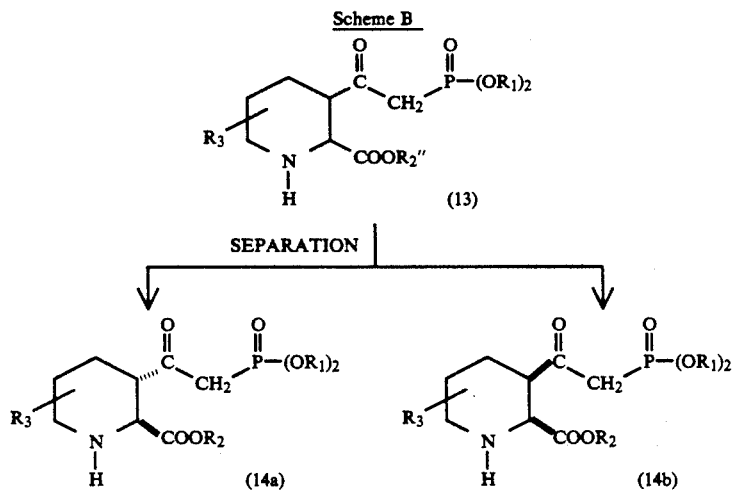

Scheme B provides a general synthetic procedure for preparing the separate diastereomeric pairs of the saturated piperidine compounds of Formula I in which M is represented by O and R₅ is represented by hydrogen.

For example, the appropriate 3-[(functionalized phosphinyl)acetyl]piperidine-2-carboxylic acid derivative of structure (13) is separated to give the corresponding d,l-trans-3-[(functionalized phosphinyl)acetyl]piperidine-2-carboxylic acid derivative of structure (14a) and the corresponding d,l-cis-3-[(functionalized phosphinyl)acetyl]piperidine-2-carboxylic acid derivative of structure (14b) by High Performance Liquid Chromatography (HPLC).

The proper starting material for the separation is a compound of Formula I as depicated by structure (13), in which R₃, R₁, and R₂ are represented by the same substituents as are desired in the final product.

The following examples present typical syntheses as described in Scheme B. These examples are understood to be illustrative only and are not intended to limit the scope of the present invention in any way.

EXAMPLE 2 d,l-trans-3-(Phosphonoacetyl)piperidine-2-carboxylic acid and
d,l-cis-3-(Phosphonoacetyl)piperidine-2-carboxylic acid

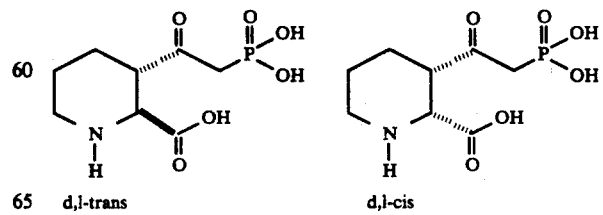

The chromatographic conditions for the separation of d,l-trans-3-(phosphonoacetyl)piperidine-2-carboxylic acid and d,l-cis-3-(phosphonoacetyl)piperidine-2-carboxylic acid are given below:

Column: 10-um Whatman Partisil SAX (250×4.6 nm).
Mobile Phase: 10/90 (v/v) acetonitrile/water, made 0.025M in hydrochloric acid.
Flow Rate: 1 mL/min.
Detection: $\lambda = 210$ nm
Injection: 2 mL of a 1 mg/mL aqueous solution Collect the fractions corresponding to the diastereomers using switching valves down stream from the detector. These valves are controlled by the HPLC system. Freeze dry the collected fractions to give the separated title compounds.

d,l-trans-3-(Phosphonoacetyl)piperidine-2-carboxylic acid $^1$H-NMR (300 MHz, NaOD) ppm 3.16 (d, J=9.9), 3.10 (m), 3.04 (m), 2.98 (m), 2.78 (m), 2.55 (t, J=12.1), 2.14 (dm, J=12.4), 1.68 (dm, J=12.3), 1.56 (qm, J=12.4), 1.46 (m).

d,l-cis-3-(Phosphonoacetyl)piperidine-2-carboxylic acid $^1$H-NMR (300 MHz, D$_2$O) ppm 3.78 (d, 1), 3.69 (m, 1), 3.38 (m, 1), 3.22-2.93 (m, 3), 2.32 (m, 1), 1.95 (m, 1), 1.79 (m, 1), 1.52 (m, 1).

Those saturated piperidine compounds of Formula I in which M is represented by either an oxime or a hydrazone derivative and R$_5$ is represented by hydrogen can also be prepared using techniques known in the art. One method for preparing these compounds is disclosed below in Scheme C. In Scheme C, all substituents unless otherwise indicated are as previously defined.

mula I in which M is represented by an oxime or a hydrazone derivative and R$_5$ is represented by hydrogen.

In step a, a condensation reaction is carried out between the appropriate 3-[(functionalized phosphinyl)acetyl]piperidine-2-carboxylic acid derivative of structure (13) in which R$_1$, R$_2$, and R$_3$ are represented by the same substituents as is desired in the final product, and in which M is O as is depicted, and one of the oximes or hydrazones of structure (15) corresponding to the M substituent that is desired in the final product. The condensation reaction can be carried out using techniques known in the art. Typically approximately equivalent amounts of the compound of Formula I and the oxime or hydrazone of structure (15) are contacted in a buffered solution. Sodium acetate is one suitable buffer. The reaction is typically carried out at a temperature range of from 25° to 80° C. for a period of time ranging from 1 to 24 h. The desired 3-[1-imino-2-phosponoethyl]piperidine-2-carboxylic acid derivative of structure (16) can then be recovered from the reaction and purified by either gel filtration or ion exchange chromatography.

In optional step b, the diastereomeric pairs of the appropriate 3-[1-imino-2-phosponoethyl]piperidine-2-carboxylic acid derivative of structure (16) are separated to give the d,l,trans-3-[1-imino-2-phosponoethyl]piperidine-2-carboxylic acid derivative of structure (17a) and d,l-cis-3-[1-imino-2-phosponoethyl]piperidine-2-carboxylic acid derivative of structure (17b) as described previously in Scheme B.

Starting materials for use in Scheme C are readily available to one of ordinary skill in the art.

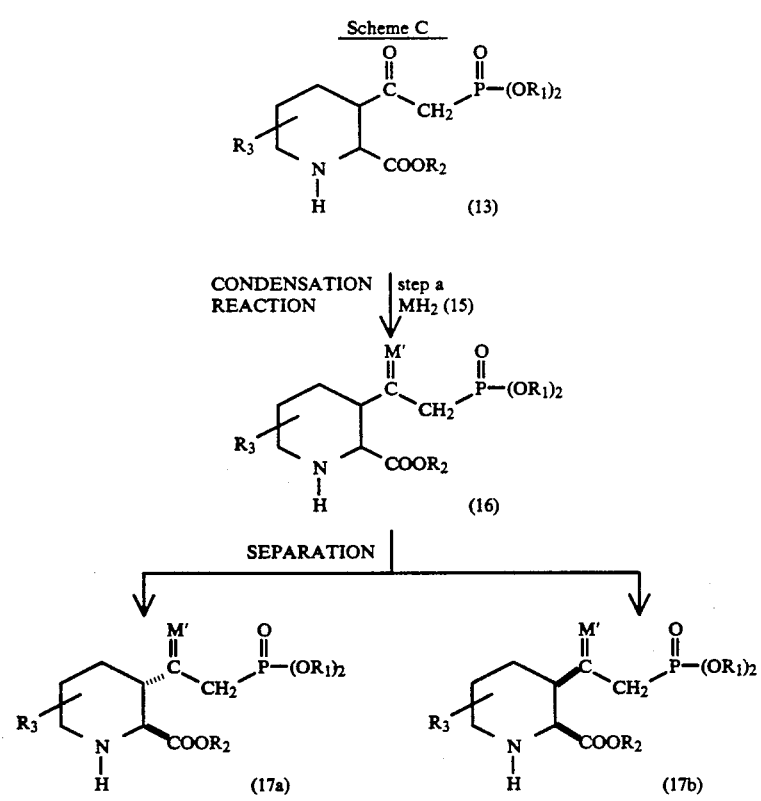

Scheme C provides a general synthetic procedure for preparing the saturated piperidine compounds of For- A synthesis for the enatiomerically pure 2(R)-, 3(S)-saturated piperidine compounds of Formula I wherein R₅ is represented by hydrogen is described in Scheme D. In Scheme D, all substituents unless otherwise indicated is as previously defined.

Scheme D provides an alternative synthetic scheme for preparing the enatiomerically pure 2(R)-, 3(S)-saturated piperidine compounds of Formula I wherein R₅ is represented by hydrogen.

In step a, the appropriate pyridine-2,3-dicarboxylic acid derivative of structure (1) is protected to give the corresponding pyridine-2,3-dicarboxylic acid, diester derivative of structure (18).

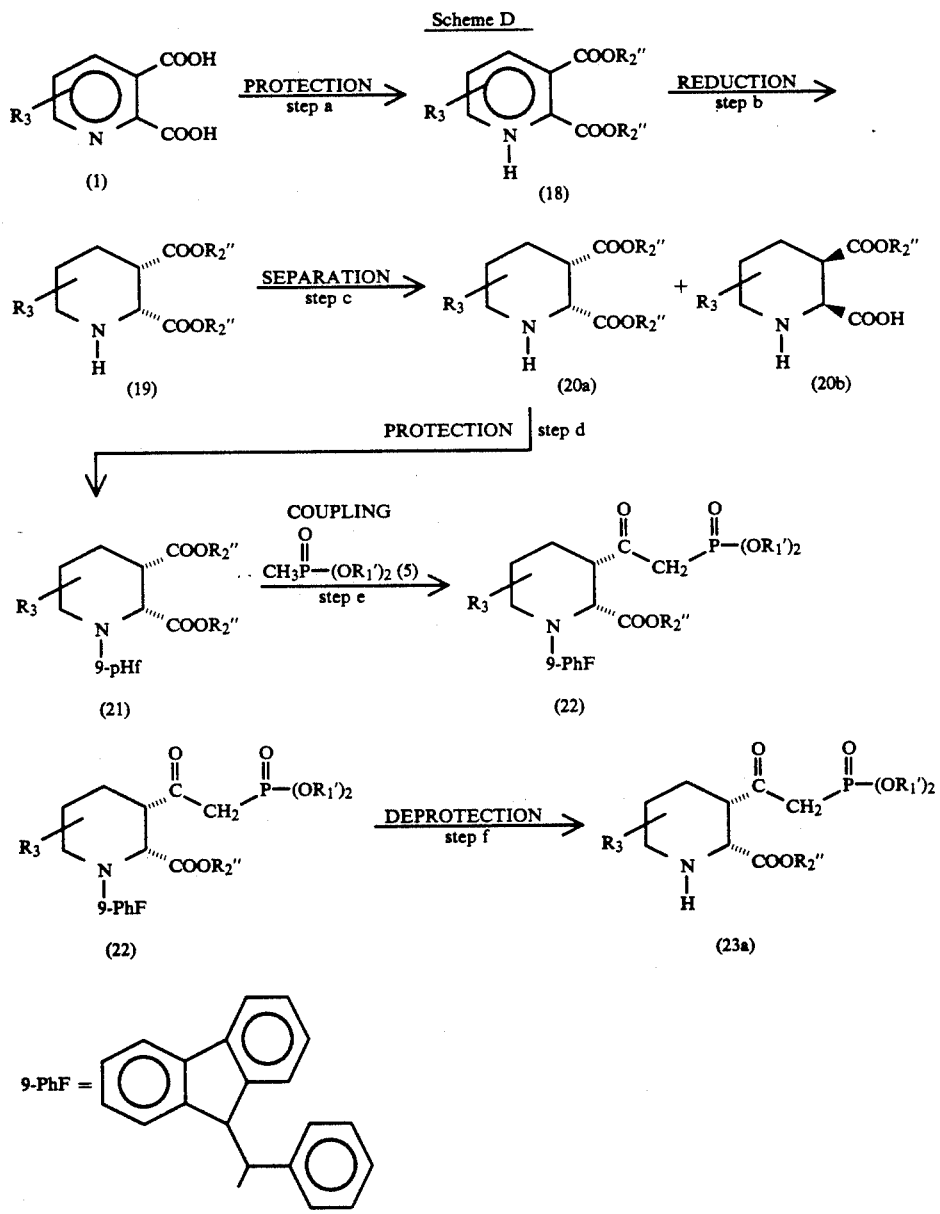

For example, the appropriate pyridine-2,3-dicarboxylic acid derivative of structure (1) is contacted with a molar excess of the appropriate alcoholic hydrochloric acid. The reactants are typically stirred together for a period of time ranging from 2-24 hours and at a temperature range of from room temperature to reflux. The pyridine-2,3-dicarboxylic acid, diester derivative of structure (18) is recovered from the reaction zone by evaporation of the solvent.

In step b, the appropriate pyridine-2,3-dicarboxylic acid, diester derivative of structure (18) is reduced to give the corresponding d,l-cis-piperidine-2,3-dicarboxylic acid, diester derivative of structure (19).

For example, the appropriate pyridine-2,3-dicarboxylic acid, diester derivative of structure (18) is contacted with an appropriate reducing agent such as palladium hydroxide in the presence of hydrogen. The reactants are typically contacted in a suitable organic solvent such as methanol. The reactants are typically shaken together at a pressure of 45–50 psi for a period of time ranging from 6 hours to 5 days and at a temperature range of from 20°–38° C. The d,l-cis-piperidine-2,3-dicarboxylic acid, diester derivative of structure (19) is recovered from the reaction zone by evaporation of the solvent.

In step c, the appropriate d,l-cis-piperidine-2,3-dicarboxylic acid, diester derivative of structure (19) is separated via an enzymatic hydrolysis into the corresponding enantiomerically pure piperidine-2(R),3(S)-dicarboxylic acid, diester derivative of structure (20a) and piperidine-2(S)-carboxylic acid-3(R)-carboxylic acid, monoester derivative of structure (20b).

For example, the appropriate d,l-cis-piperidine-2,3-dicarboxylic acid, diester derivative of structure (19) is contacted with a molar excess of a suitable esterase such as porcine liver esterase. The reactants are typically contacted in a suitable buffered solvent system such as pH 7.4 phosphate buffer. The reactants are typically stirred together at room temperature for a period of time ranging from 10–48 hours. The enantiomerically pure piperidine-2(R),3(S)-dicarboxylic acid, diester derivative of structure (20a) is recovered from the reaction mixture by extractive methods as is known in the art and the enantiomerically pure piperidine-2(S)-carboxylic acid-3(R)-carboxylic acid, monoester derivative of structure (20b) can be recovered from the reaction zone ion-exchange chromatography.

In step d, the appropriate piperidine-2(R),3(S)-dicarboxylic acid, diester derivative of structure (20a) is protected to give the corresponding N-protected-piperidine-2(R),3(S)-dicarboxylic acid, diester derivative of structure (21) as described previously in Scheme A, step b.

In step e, the appropriate N-protected-piperidine-2(R),3(S)-dicarboxylic acid, diester derivative of structure (21) is coupled with an appropriate phosphonate ester of structure (5) to give the corresponding N-protected-3(S)-[(dialkoxyphosphinyl)acetyl]piperidine-2(R)-carboxylic acid, ester of structure (22) as described previously in Scheme A, step d.

In step f, the N-protecting group of the appropriate N-protected-3(S)-[(dialkoxyphosphinyl)acetyl]piperidine-2(R)-carboxylic acid, ester of structure (22) is removed to give the corresponding 3(S)-[(dialkoxyphosphinyl)acetyl]piperidine-2(R)-carboxylic acid, ester of structure (23a) as described previously in Scheme A, step f.

The appropriate 3(S)-[(dialkoxyphosphinyl)acetyl]-piperidine-2(R)-carboxylic acid, ester of structure (23a) can be further functionalized as described previously in Scheme A, steps $g_1$-i.

The appropriate 3(S)-[(functionalized phosphinyl)acetyl]piperidine-2(R)-carboxylic acid derivatives of Formula I prepared as described above in Scheme D may also be further functionalized into the corresponding 3(S)-[1-imino-2-phosponoethyl]piperidine-2(R)-carboxylic acid derivatives of Formula I as described previously in Scheme C, step a.

Starting materials for use in Scheme D are readily available to one of ordinary skill in the art.

The following examples present typical syntheses as described in Scheme D. These examples are intended to be illustrative only and are not intended to limit the scope of the present invention in any way.

EXAMPLE 3

3(S)-[(Diethoxyphosphinyl)acetyl]piperidine-2(R)-carboxylic acid, methyl ester

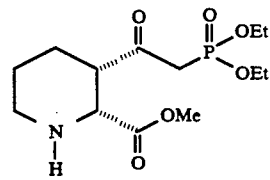

Step a: Pyridine-2,3-dicarboxylic acid, dimethyl ester

Dissolve pyridine-2,3-dicarboxylic acid (100 g) in methanol (1.25 L). Bubble in HCl gas until a solution is obtained. Reflux overnight, evaporate the solvent in vacuo and neutralize with saturated aqueous sodium hydrogen carbonate in ethyl acetate. Separate the organic phase, dry (MgSO$_4$) and evaporate the solvent in vacuo to give the title compound as a white solid (96.1 g).

$^1$H NMR (90 MHz, CDCl$_3$) ppm 8.6 (m, 1), 8.05 (m, 1), 7.4 (m, 1), 3.9 (s, 3), 3.8 (s, 3).

Step b: d,l-cis-Piperidine-2,3-dicarboxylic acid, dimethyl ester

Dissolve pyridine-2,3-dicarboxylic acid, dimethyl ester (19 g) in methanol (500 mL) and treat with 20% palladium hydroxide/carbon (1.5 g). Place on a Paar Hydrogenation Apparatus and hydrogenate at 50 psi for 6 hours. Filter and evaporate the solvent in vacuo to give the title compound (14 g).

$^1$H NMR (300 MHz, CDCl$_3$) ppm 3.76 (s, 3), 3.70 (s, 3), 3.66 (d, 1), 3.06 (m, 1), 2.99 (m, 1), 2.7 (m, 1), 2.24–2.1 (m, 2), 1.79 (m, 1), 1.5 (m, 2).

Step c: Piperidine-2(R),3(S)-dicarboxylic acid, dimethyl ester and Piperidine-2(S)-carboxylic acid-3(R)-carboxylic acid, monomethyl ester Dissolve d,l-cis-piperidine-2,3-dicarboxylic acid, dimethyl ester (75 mg) in pH 7.4 phosphate buffer (1.5 mL) and shake for 24 hours in the presence of porcine liver esterase. Evaporate to a residue, stir with ethyl acetate and filter. Evaporate the solvent in vacuo to give the title dimethyl ester compound.

Alternatively, extract the residue with water and purify by ion-exchange chromatography to give the title monoester compound.

Step d: N-(9-Phenylfluorenyl)piperidine-2(R),3(S)-dicarboxylic acid, dimethyl ester Dissolve piperidine-2(R),3(S)-dicarboxylic acid, dimethyl ester (5.0 g, 24.8 mmol) and diisopropylethylamine (3.5 g, 41.8 mmol) in acetonitrile (90 mL) and add 4A molecular sieves. Add phenylfluorenyl bromide (8.8 g, 27.3 mmol) and lead nitrate (8.2 g, 24.8 mmol). Stir at room temperature under an argon atmosphere overnight. Add methylene chloride (150 mL) and filter through celite. Wash the filtrate with saturated aqueous sodium hydrogen carbonate (2×) and saturated sodium chloride. Dry (MgSO$_4$), evaporate the solvent in vacuo and recrystallize (methylene chloride/hexane) to give the title compound.

Step e: N-(9-Phenylfluorenyl)-3(S)-[(diethoxyphosphinyl)acetyl]piperidine-2(R)-carboxylic acid, methyl ester Dissolve diethyl methylphosphate (2.28 g, 15 mmol) in anhydrous tetrahydrofuran (10 mL), cool to −78° C. and place under an argon atmosphere. Add, by dropwise addition, n-butyllithium (8 mL of a 1.6M solution, 15 mmol). Stir for 20 minutes at −78° C. and add a solution of N-(9-phenylfluorenyl)piperidine-2(R),3(S)-dicarboxylic acid, dimethyl ester (2.21 g, 5 mmol) in anhydrous tetrahydrofuran (5 mL). Stir for ½ hour at −78° C., quench with acetic acid (2 mL) and warm to room temperature. Quench with water (50 mL) and extract into ethyl acetate (100 mL). Evaporate the solvent in vacuo to give a residue. Purify by silica gel chromatography to give the title compound.

Step f: 3(S)-[(Diethoxyphosphinyl)acetyl]piperidine-2(R)-carboxylic acid, methyl ester Dissolve N-(9-phenylfluorenyl)-3(S)-[(diethoxyphosphinyl)acetyl]piperidine-2(R)-carboxylic acid, ethyl ester (1 g) in acetonitrile (7 mL) and water (1 mL). Cool to 0° C. and add, by dropwise addition, trifluoroacetic acid (7 mL). Stir at 0° C. for 1 hour then warm to room temperature over 1 hour. Extract into ethyl acetate (10×100 mL) and evaporate the solvent in vacuo to give the title compound.

EXAMPLE 4

3(S)-[(Diethoxyphosphinyl)acetyl]piperidine-4-methyl-2(R)-carboxylic acid, methyl ester and 3(R)-[(Diethoxyphosphinyl)acetyl]piperidine-4-methyl-2(S)-carboxylic acid, methyl ester

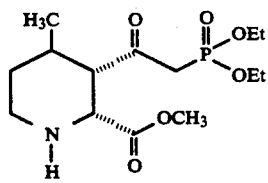

Step a: Pyridine-4-methyl-2,3-dicarboxylic acid, dimethyl ester

Dissolve pyridine-4-methyl-2,3-dicarboxylic acid (100 g) in methanol (1.25 L). Bubble in HCl gas until a solution is obtained. Reflux overnight, evaporate the solvent in vacuo and neutralize with saturated aqueous sodium hydrogen carbonate in ethyl acetate. Separate the organic phase, dry (MgSO$_4$) and evaporate the solvent in vacuo to give the title compound.

Step b: d,l-cis-Piperidine-4-methyl-2,3-dicarboxylic acid, dimethyl ester

Dissolve pyridine-4-methyl-2,3-dicarboxylic acid, dimethyl ester (19 g) in methanol (500 mL) and treat with 20% palladium hydroxide/carbon (1.5 g). Place on a Paar Hydrogenation Apparatus and hydrogenate at 50 psi for 6 hours. Filter and evaporate the solvent in vacuo to give the title compound.

Step c: Piperidine-4-methyl-2(R),3(S)-dicarboxylic acid, dimethyl ester and Piperidine-4-methyl-2(R)-carboxylic acid-3(S)-carboxylic acid, monomethyl ester and Piperidine-4-methyl-2(S),3(R)-dicarboxylic acid, dimethyl ester and Piperidine-4-methyl-2(S)-carboxylic acid-3(R)-carboxylic acid, monomethyl ester Dissolve d,l-cis-piperidine-4-methyl-2,3-dicarboxylic acid, dimethyl ester (75 mg) in pH 7.4 phosphate buffer (1.5 mL) and shake for 24 hours in the presence of porcine liver esterase. Evaporate to a residue, stir with ethyl acetate and filter. Evaporate the solvent in vacuo to give the title diester compounds.

Alternatively, extract the residue with water and purify by ion-exchange chromatography to give the title monoester compounds.

Step d: N-(9-Phenylfluorenyl)piperidine-4-methyl-2(R),3(S)-dicarboxylic acid, dimethyl ester and N-(9-Phenylfluorenyl)piperidine-4-methyl-2(S),3(R)-dicarboxylic acid, dimethyl ester Dissolve the mixture of piperidine-4-methyl-2(R),3(S)-dicarboxylic acid, dimethyl ester and piperidine-4-methyl-2(S),3(R)-dicarboxylic acid, dimethyl ester (5.33 g, 24.8 mmol) and diisopropylethylamine (3.5 g, 41.8 mmol) in acetonitrile (90 mL). Add phenylfluorenyl bromide (8.8 g, 27.3 mmol) and lead nitrate (8.2 g, 24.8 mmol). Stir at room temperature under an argon atmosphere overnight. Add methylene chloride (150 mL) and filter through celite. Wash the filtrate with saturated aqueous sodium hydrogen carbonate (2×) and saturated sodium chloride. Dry (MgSO$_4$), evaporate the solvent in vacuo and purify by silica gel chromatography to give the title compound.

Step e: N-(9-Phenylfluorenyl)-3(S)-[(diethoxyphosphinyl)acetyl]piperidine-4-methyl-2(R)-carboxylic acid, methyl ester and N-(9-Phenylfluorenyl)-3(R)-[(diethoxyphosphinyl)acetyl]piperidine-4-methyl-2(S)-carboxylic acid, methyl ester Dissolve diethyl methylphosphate (2.28 g, 15 mmol) in anhydrous tetrahydrofuran (10 mL), cool to −78° C. and place under an argon atmosphere. Add, by dropwise addition, n-butyllithium (8 mL of a 1.6M solution, 15 mmol). Stir for 20 minutes at −78° C. and add a solution of the mixture of N-(9-phenylfluorenyl)piperidine-4-methyl-2(R),3(S)-dicarboxylic acid, dimethyl ester N-(9-phenylfluorenyl)piperidine-4-methyl-2(S),3(R)-dicarboxylic acid, dimethyl ester (2.35 g, 5 mmol) in anhydrous tetrahydrofuran (5 mL). Stir for ½ hour at −78° C., quench with acetic acid (2 mL) and warm to room temperature. Quench with water (50 mL) and extract into ethyl acetate (100 mL). Evaporate the solvent in vacuo to give a residue. Purify by silica gel chromatography to give the title compounds.

Step f:
3(S)-[(Diethoxyphosphinyl)acetyl]piperidine-4-methyl-2(R)-carboxylic acid, methyl ester and
3(R)-[(Diethoxyphosphinyl)acetyl]piperidine-4-methyl-2(S)-carboxylic acid, methyl ester Dissolve the mixture of N-(9-phenylfluorenyl)-3(S)-[(diethoxyphosphinyl)acetyl]piperidine-4-methyl-2(R)-carboxylic acid, methyl ester N-(9-phenylfluorenyl)-3(R)-[(diethoxyphosphinyl)acetyl]piperidine-4-methyl-2(S)-carboxylic acid, methyl ester (1 g) in acetonitrile (7 mL) and water (1 mL). Cool to 0° C. and add, by dropwise addition, trifluoroacetic acid (7 mL). Stir at 0° C. for 1 hour then warm to room temperature over 1 hour. Extract into ethyl acetate (10×100 mL) and evaporate the solvent in vacuo to give the title compound.

EXAMPLE 5

3(S)-(Phosphonoacetyl)piperidine-4-methyl-2(R)-carboxylic acid and
3(R)-(Phosphonoacetyl)piperidine-4-methyl-2(S)-carboxylic acid

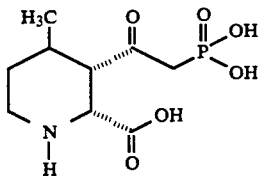

Dissolve the mixture of 3(S)-[(diethoxyphosphinyl)acetyl]piperidine-4-methyl-2(R)-carboxylic acid, methyl ester and 3(R)-[(diethoxyphosphinyl)acetyl]piperidine-4-methyl-2(S)-carboxylic acid, methyl ester (3 g) in acetonitrile (20 mL) and methylene chloride (20 mL). Add trimethylsilyl iodide (3.5 mL, 24 mmol) and stir for 5 hours. Pour into water (250 mL) and wash with toluene (3×250 mL). Freeze dry the aqueous phase to give a solid residue. Take up the solid residue in methanol (10 mL) and isopropanol (5 mL). Add propylene oxide (2 mL) and stir for 1 hour. Filter to give the title compound.

EXAMPLE 6

3(S)-[(Diethoxyphosphinyl)acetyl]piperidine-5-methyl-2(R)-carboxylic acid, methyl ester

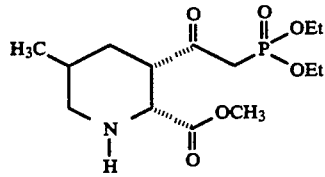

Step a: Pyridine-5-methyl-2,3-dicarboxylic acid, dimethyl ester

Dissolve pyridine-5-methyl-2,3-dicarboxylic acid (100 g) in methanol (1.25 L). Bubble in HCl gas until a solution is obtained. Reflux overnight, evaporate the solvent in vacuo and neutralize with saturated aqueous sodium hydrogen carbonate in ethyl acetate. Separate the organic phase, dry (MgSO4) and evaporate the solvent in vacuo to give the title compound.

Step b: d,l-cis-Piperidine-5-methyl-2,3-dicarboxylic acid, dimethyl ester

Dissolve pyridine-5-methyl-2,3-dicarboxylic acid, dimethyl ester (19 g) in methanol (500 mL) and treat with 20% palladium hydroxide/carbon (1.5 g). Place on a Paar Hydrogenation Apparatus and hydrogenate at 50 psi for 6 hours. Filter and evaporate the solvent in vacuo to give the title compound.

Step c: Piperidine-5-methyl-2(R),3(S)-dicarboxylic acid, dimethyl ester and
Piperidine-5-methyl-2(R)-carboxylic acid-3(S)-carboxylic acid, monomethyl ester Dissolve d,l-cis-piperidine-5-methyl-2,3-dicarboxylic acid, dimethyl ester (75 mg) in pH 7.4 phosphate buffer (1.5 mL) and shake for 24 hours in the presence of porcine liver esterase. Evaporate to a residue, stir with ethyl acetate and filter. Evaporate the solvent in vacuo to give the title compound.

Alternatively, extract the residue with water and purify by ion-exchange chromatography to give the title monoester compounds.

Step d:
N-(9-Phenylfluorenyl)piperidine-5-methyl-2(R),3(S)-dicarboxylic acid, dimethyl ester Dissolve piperidine-5-methyl-2(R),3(S)-dicarboxylic acid, dimethyl ester (5.33 g, 24.8 mmol) and diisopropylethylamine (3.5 g, 41.8 mmol) in acetonitrile (90 mL). Add phenylfluorenyl bromide (8.8 g, 27.3 mmol) and lead nitrate (8.2 g, 24.8 mmol). Stir at room temperature under an argon atmosphere overnight. Add methylene chloride (150 mL) and filter through celite. Wash the filtrate with saturated aqueous sodium hydrogen carbonate (2×) and saturated sodium chloride. Dry (MgSO4), evaporate the solvent in vacuo and purify by silica gel chromatography to give the title compound.

Step e:
N-(9-Phenylfluorenyl)-3(S)-[(diethoxyphosphinyl)acetyl]piperidine-5-methyl-2(R)-carboxylic acid, methyl ester Dissolve diethyl methylphosphate (2.28 g, 15 mmol) in anhydrous tetrahydrofuran (10 mL), cool to −78° C. and place under an argon atmosphere. Add, by dropwise addition, n-butyllithium (8 mL of a 1.6M solution, 15 mmol). Stir for 20 minutes at −78° C. and add a solution of N-(9-phenylfluorenyl)piperidine-5-methyl-2(R),3(S)-dicarboxylic acid, dimethyl ester (2.35 g, 5 mmol) in anhydrous tetrahydrofuran (5 mL). Stir for ½ hour at −78° C., quench with acetic acid (2 mL) and warm to room temperature. Quench with water (50 mL) and extract into ethyl acetate (100 mL). Evaporate the solvent in vacuo to give a residue. Purify by silica gel chromatography to give the title compound.

Step f:
3(S)-[(Diethoxyphosphinyl)acetyl]piperidine-5-methyl-2(R)-carboxylic acid, methyl ester Dissolve N-(9-phenylfluorenyl)-3(S)-[(diethoxyphosphinyl)acetyl]piperidine-5-methyl-2(R)-carboxylic acid, methyl ester (1 g) in acetonitrile (7 mL) and water (1 mL). Cool to 0° C. and add, by dropwise addition, trifluoroacetic acid (7 mL). Stir at 0° C. for 1 hour then warm to room temperature over 1 hour. Extract into ethyl acetate (10×100 mL) and evaporate the solvent in vacuo to give the title compound.

EXAMPLE 7

3(S)-(Phosphonoacetyl)piperidine-5-methyl-2(R)-carboxylic acid

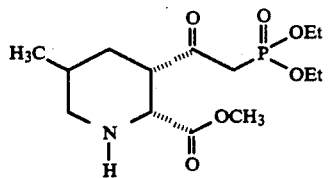

Dissolve the mixture of 3(S)-[(diethoxyphosphinyl-)acetyl]piperidine-5-methyl-2(R)-carboxylic acid, methyl ester (3g) in acetonitrile (20 mL) and methylene chloride (20 mL). Add trimethylsilyl iodide (3.5 mL, 24 mmol) and stir for 5 hours. Pour into water (250 mL) and wash with toluene (3×250 mL). Freeze dry the aqueous phase to give a solid residue. Take up the solid residue in methanol (10 mL) and isopropanol (5 mL). Add propylene oxide (2 mL) and stir for 1 hour. Filter and dry to give the title compound.

An alternative synthetic procedure for preparing the d,l-cis or the enatiomerically pure 2(R),3(S) and 2(S),3(R) saturated piperidine compounds of Formula I wherein $R_5$ is represented by hydrogen is described in Scheme E. In Scheme E all substituents unless otherwise indicated are as previously defined.

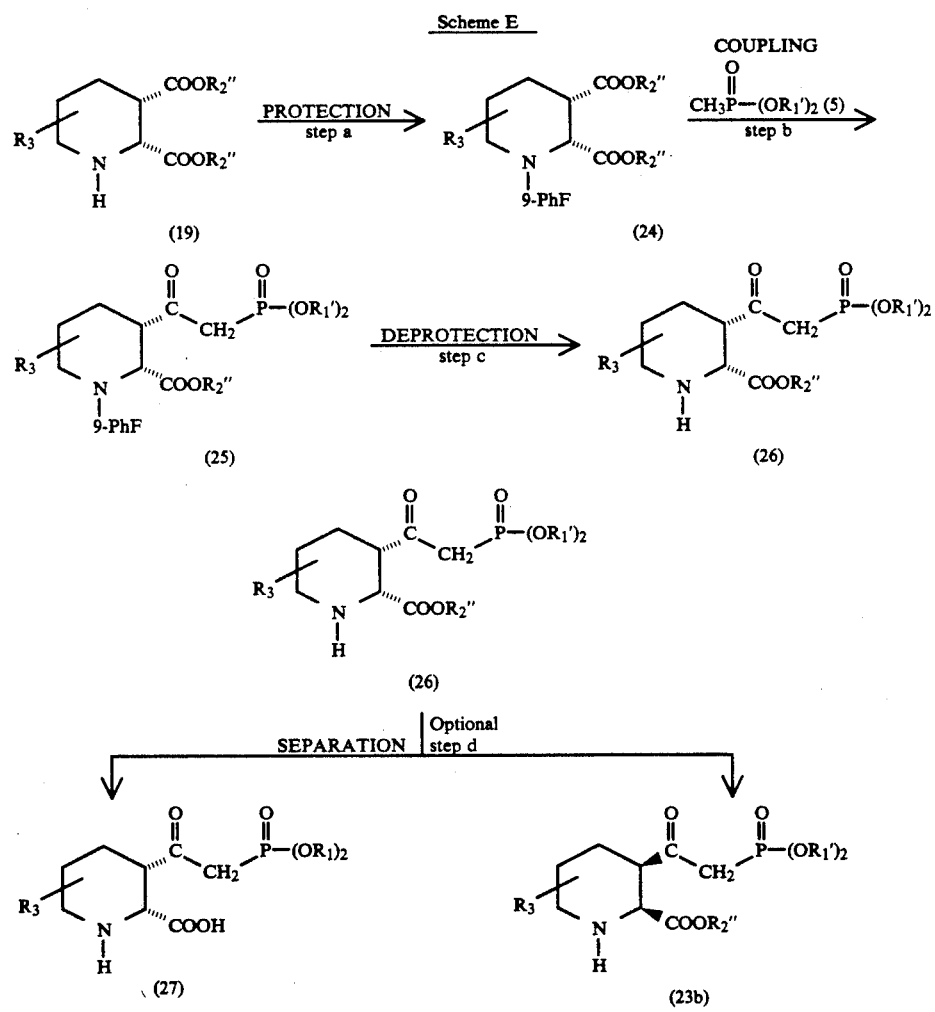

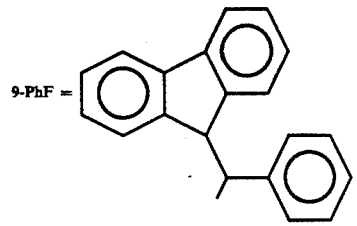

$R_2'' = -CH_3$ or $-CH_2CH_3$
$R_1' = C_1-C_4$ alkyl or $CF_3$

Scheme E provides an alternative general synthetic procedure for preparing the d,l-cis or the enatiomerically pure 2(R),3(S) and 2(S),3(R) saturated piperidine compounds of Formula I wherein $R_5$ is represented by hydrogen.

In step a, the appropriate d,l-cis-piperidine-2,3-dicarboxylic acid, diester derivative of structure (19) is protected to give the corresponding d,l-cis-N-protected-piperidine-2,3-dicarboxylic acid, diester derivative of structure (24) as described previously in Scheme A, step b.

In step b, the appropriate d,l-cis-N-protected-piperidine-2,3-dicarboxylic acid, diester derivative of structure (24) is coupled with the appropriate phosphonate ester of structure (5) to give the corresponding d,l-cis-N-protected-3-[(dialkoxyphosphinyl)acetyl]piperidine-2-carboxylic acid, ester of structure (25) as described previously in Scheme A, step d.

In step c, the appropriate d,l-cis-N-protected-3-[(dialkoxyphosphinyl)acetyl]piperidine-2-carboxylic acid, ester of structure (25) is deprotected to give the corresponding d,l-cis-3-[(dialkoxyphosphinyl)acetyl]piperidine-2-carboxylic acid, ester of structure (26) as described previously in Scheme A, step f.

In optional step d, the appropriate d,l-cis-3-[(dialkoxyphosphinyl)acetyl]piperidine-2-carboxylic acid, ester of structure (26) is separated to give the corresponding 3(S)-[(dialkoxyphosphinyl)acetyl]piperidine-2(R)-carboxylic acid of structure (27) and the 3(R)-[(dialkoxyphosphinyl)acetyl]piperidine-2(S)-carboxylic acid, ester of structure (23b) as described previously in Scheme D, step c.

The appropriate 3(S)-[(dialkoxyphosphinyl)acetyl]-piperidine-2(R)-carboxylic acid of structure (27) can be further functionalized as described previously in Scheme A, steps $g_1$ and steps $h_1$-i.

The appropriate 3(R)-[(dialkoxyphosphinyl)acetyl]-piperidine-2(S)-carboxylic acid, ester of structure (23b) can be further functionalized as described previously in Scheme A, steps $g_1$-i.

The appropriate d,l-cis-3-[(functionalized phosphinyl)acetyl]piperidine-2-carboxylic acid derivatives, 3(S)-[(functionalized phosphinyl)acetyl]piperidine-2(R)-carboxylic acid derivatives and 3(R)-[(functionalized phosphinyl)acetyl]piperidine-2(S)-carboxylic acid derivatives of Formula I prepared as described above in Scheme E may also be further functionalized into the corresponding d,l-cis-3-[1-imino-2-phosponoethyl]-piperidine-2-carboxylic acid derivatives, 3(S)-[1-imino-2-phosponoethyl]piperidine-2(R)-carboxylic acid derivatives and 3(R)-[1-imino-2-phosponoethyl]piperidine-2(S)-carboxylic acid derivatives of Formula I as described previously in Scheme C, step a.

Starting materials for use in Scheme E are readily available to one of ordinary skill in the art.

The following examples present typical syntheses as described in Scheme E. These examples are intended to be illustrative only and are not intended to limit the scope of the present invention in any way.

EXAMPLE 8 d,l-cis-3-[(Diethoxyphosphinyl)acetyl]piperidine-2-carboxylic acid, methyl ester

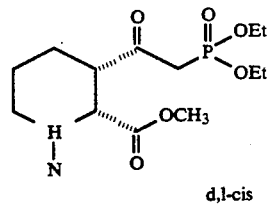

d,l-cis

Step a:
d,l-cis-N-(9-Phenylfluorenyl)piperidine-2,3-dicarboxylic acid, diethyl ester Dissolve d,l-cis-piperidine-2,3-dicarboxylic acid, diethyl ester (5.0 g, 24.8 mmol) and diisopropylethylamine (3.5 g, 41.8 mmol) in acetonitrile (90 mL). Add phenylfluorenyl bromide (8.8 g, 27.3 mmol) and lead nitrate (8.2 g, 24.8 mmol). Stir at room temperature under an argon atmosphere overnight. Add methylene chloride (150 mL) and filter through celite. Wash the filtrate with saturated aqueous sodium hydrogen carbonate (2×) and saturated sodium chloride. Dry (MgSO$_4$) and evaporate the solvent in vacuo to give 12.5 g red foam. Purify by silica gel chromatography (9:1 hexane/ethyl ether to 7:3 hexane/ethyl ether) to give the title compound as a white solid (8.7 g); mp 177°–177.5° C. (hexane/ethyl ether).

Step b:
d,l-cis-N-(9-Phenylfluorenyl)-3-[(diethoxyphosphinyl)acetyl]piperidine-2-carboxylic acid, ethyl ester Dissolve diethyl methylphosphate (2.28 g, 15 mmol) in anhydrous tetrahydrofuran (10 mL), cool to −78° C. and place under an argon atmosphere. Add, by dropwise addition, n-butyllithium (8 mL of a 1.6M solution, 15 mmol). Stir for 20 minutes at −78° C. and add a solution of d,l-cis-N-(9-phenylfluorenyl)piperidine-2,3-dicarboxylic acid, diethyl ester (2.21 g, 5 mmol) in anhydrous tetrahydrofuran (5 mL). Stir for ½ hour at −78° C., quench with acetic acid (2 mL) and warm to room temperature. Quench with water (50 mL) and extract into ethyl acetate (100 mL). Evaporate the solvent in vacuo to give a residue. Recrystallize the residue (ethyl acetate) to give 0.8 g of a white solid. Purify by silica gel chromatography (ethyl acetate) to give the title compound (0.5 g).

$^1$H NMR (300 MHz, CDCl$_3$) ppm 7.69 (dd, 2), 7.15–7.45 (m, 9), 4.1 (m, 4), 3.78 (d, ?), 3.49 (dt, 1), 2.95–3.3 (m, 4), 2.85 (s, 3), 1.7–2.15 (m, 4), 1.3 (m, 6).

Step c:
d,l-cis-3-[(Diethoxyphosphinyl]acetyl]piperidine-2-carboxylic acid, ethyl ester Dissolve d,l-cis-N-(9-phenylfluorenyl)-3-[(diethoxyphosphinyl)acetyl]piperidine-2-carboxylic acid, ethyl ester (1 g) in acetonitrile (7 mL) and water (1 mL). Cool to 0° C. and add, by dropwise addition, trifluoroacetic acid (7 mL). Stir at 0° C. for 1 hour then warm to room temperature over 1 hour. Extract into ethyl acetate (10×100 mL) and evaporate the solvent in vacuo to give the title compound.

1H NMR (300 MHz, CDCl3) ppm 4.15 (m, 4), 3.71 (m, 1), 3.69 (s, 3), 2.9-3.4 (m, 4), 2.70 (m, 1), 1.9-2.2 (m, 4), 1.5 (m, 2), 1.32 (m, 6).

An alternative synthetic procedure for preparing the enantiomerically pure 2(R),3(S) saturated piperidine compounds of Formula I wherein $R_5$ is represented by hydrogen is set forth in Scheme F. In Scheme F, all substituents unless otherwise indicated are as previously defined.

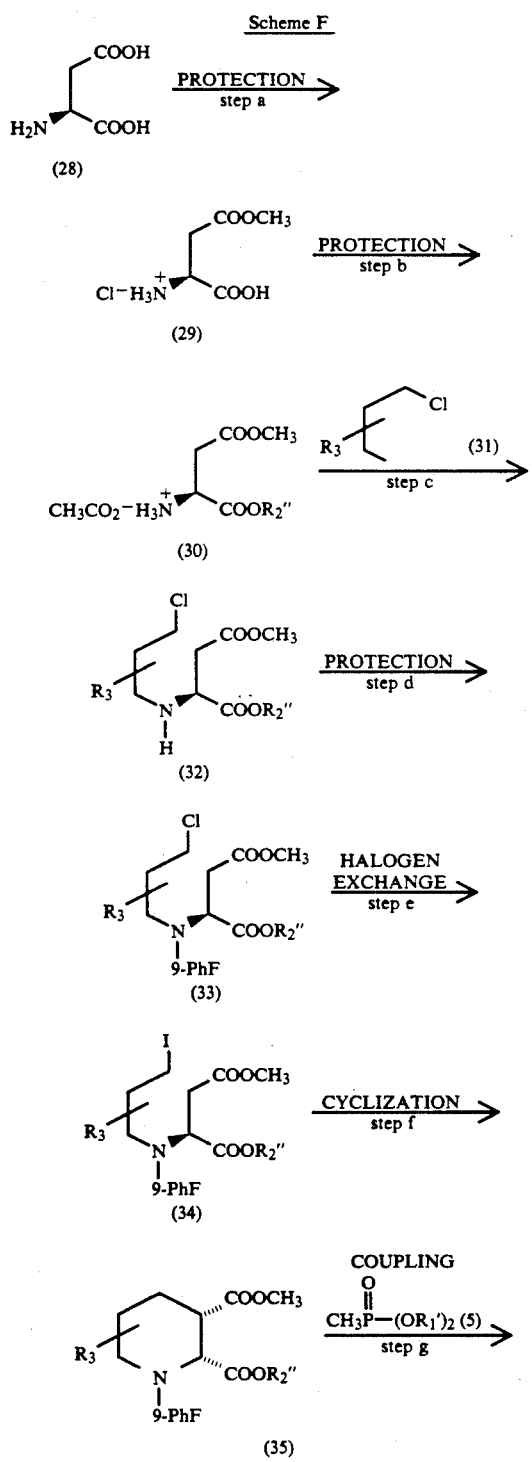

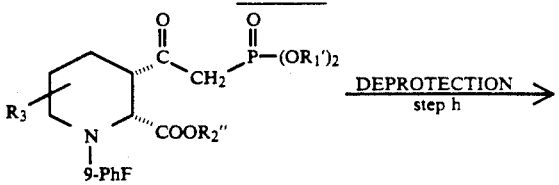

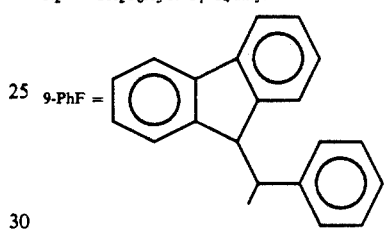

$R_1' = C_1-C_4$ alkyl or $CF_3$
$R_2'' = CH_2C_6H_5$ or $C_1-C_4$ alkyl

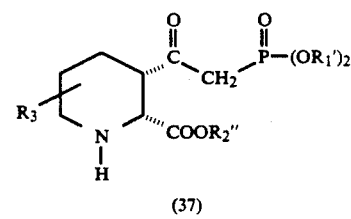

9-PhF =

Scheme F provides an alternative general synthetic procedure for preparing the enantiomerically pure 2(R),3(S) saturated piperidine compounds of Formula I wherein $R_5$ is represented by hydrogen.

In step a, D-aspartic acid (28) is protected to give the corresponding β-methyl-D-aspartate (29) as described previously in Scheme D, step a.

In step b, β-methyl-D-aspartate (29) is protected to give the corresponding α-$C_1-C_4$ alkyl or benzyl-β-methyl-D-aspartate acetic acid of structure (30) with the tert-butyl ester being preferred.

For example, β-methyl-D-aspartate (29) is contacted with a molar excess of tert-butyl acetate and a slight molar excess of an appropriate acid such as perchloric acid. The reactants are typically stirred together at room temperature for a period of time ranging from 1-24 hours. The α-tert-butyl-β-methyl-D-aspartate acetic acid of structure (30) is recovered from the reaction zone by extractive methods as is known in the art.

In step c, the appropriate α-$C_1-C_4$ alkyl or benzyl-β-methyl-D-aspartate acetic acid of structure (30) is alkylated with the appropriate 1-bromo-3-chloropropane of structure (31) to give the corresponding α-$C_1-C_4$ alkyl or benzyl-β-methyl-N-(3-chloropropyl)-D-aspartate of structure (32).

For example, the appropriate α-$C_1-C_4$ alkyl or benzyl-β-methyl-D-aspartate acetic acid of structure (30) is contacted with a molar equivalent of an appropriate 1-bromo-3-chloropropane of structure (31) and a molar excess of an appropriate base such as triethylamine. The reactants are typically contacted in a suitable organic solvent such as acetonitrile. The reactants are typically stirred together for a period of time ranging from 2-24 hours and at a temperature range of from room temperature to 80° C. The α-$C_1-C_4$ alkyl or benzyl-β-methyl-N-(3-chloropropyl)-D-aspartate of structure (32) is recovered from the reaction zone by extractive methods as is known in the art. It may be purified by silica gel chromatography.

The appropriate 1-bromo-3-chloropropane of structure (31) is one in which $R_3$ is the same as is desired in the final product.

In step d, the appropriate $\alpha$-$C_1$-$C_4$ alkyl or benzyl-$\beta$-methyl-N-(3-chloropropyl)-D-aspartate of structure (32) is protected to give the corresponding $\alpha$-$C_1$-$C_4$ alkyl or benzyl-$\beta$-methyl-N-(3-chloropropyl)-N-(9-phenylfluorenyl)-D-aspartate of structure (33) as described previously in Scheme A, step b.

In step e, the chloride functionality of the appropriate $\alpha$-$C_1$-$C_4$ alkyl or benzyl-$\beta$-methyl-N-(3-chloropropyl)-N-(9-phenylfluorenyl)-D-aspartate of structure (33) is exchanged to give the corresponding $\alpha$-$C_1$-$C_4$ alkyl or benzyl-$\beta$-methyl-N-(3-iodopropyl)-N-(9-phenylfluorenyl)-D-aspartate of structure (34).

For example, the appropriate $\alpha$-$C_1$-$C_4$ alkyl or benzyl-$\beta$-methyl-N-(3-chloropropyl)-N-(9-phenylfluorenyl)-D-aspartate of structure (33) is contacted with a molar excess of an iodide source, such as sodium iodide. The reactants are typically contacted in a suitable organic solvent such as acetonitrile. The reactants are typically stirred together for a period of time ranging from 2–24 hours and at a temperature range of from room temperature to 65° C. The $\alpha$-$C_1$-$C_4$ alkyl or benzyl-$\beta$-methyl-N-(3-iodopropyl)-N-(9-phenylfluorenyl)-D-aspartate of structure (34) is recovered from the reaction zone by extractive methods as is known in the art. It may be purified by recrystallization.

In step f, the appropriate $\alpha$-$C_1$-$C_4$ alkyl or benzyl-$\beta$-methyl-N-(3-iodopropyl)-N-(9-phenylfluorenyl)-D-aspartate of structure (34) is cyclized to give the corresponding N-protected-piperidine-2(R)-$C_1$-$C_4$ alkyl or benzyl ester-3(S)-methyl ester of structure (35).

For example, the appropriate $\alpha$-$C_1$-$C_4$ alkyl or benzyl-$\beta$-methyl-N-(3-iodopropyl)-N-(9-phenylfluorenyl)-D-aspartate of structure (34) is contacted with an appropriate base such as lithium diisopropylamine. The reactants are typically contacted in a suitable organic solvent such as tetrahydrofuran. The reactants are typically stirred together for a period of time ranging from 2–20 hours and at a temperature range of from −78° C. to −20° C. The N-protected-piperidine-2(R)-$C_1$-$C_4$ alkyl or benzyl ester-3(S)-methyl ester of structure (35) is recovered from the reaction zone by a low-temperature quench into an appropriate proton source, such as diisopropyl phenol, followed by acidification and extraction as is known in the art. It may be purified by silica gel chromatography.

In step g, the appropriate N-(9-phenylfluorenyl)-piperidine-2(R)-$C_1$-$C_4$ alkyl or benzyl ester-3(S)-methyl ester of structure (35) is coupled with an appropriate phosphonate ester of structure (5) to give the corresponding N-(9-phenylfluorenyl)-3(S)-[(dialkoxyphosphinyl)acetyl]piperidine-2(R)-carboxylic acid, benzyl or $C_1$-$C_4$ alkyl ester of structure (36) as described previously in Scheme A, step d.

In step h, the appropriate N-(9-phenylfluorenyl)-3(S)-[(dialkoxyphosphinyl)acetyl]piperidine-2(R)-carboxylic acid, benzyl or $C_1$-$C_4$ alkyl ester of structure (36) is deprotected to give the corresponding 3(S)-[(dialkoxyphosphinyl)acetyl]piperidine-2(R)-carboxylic acid, benzyl or $C_1$-$C_4$ alkyl ester of structure (37) as described previously in Scheme A, step f.

The appropriate 3(S)-[(dialkoxyphosphinyl)acetyl]piperidine-2(R)-carboxylic acid, benzyl or $C_1$-$C_4$ alkyl ester of structure (37) can be further functionalized as described previously in Scheme A, steps g1-i.

The appropriate 3(S)-[(functionalized phosphinyl)acetyl]piperidine-2(R)-carboxylic acid derivatives of Formula I prepared as described above in Scheme F may also be further functionalized into the corresponding 3(S)-[1-imino-2-phosponoethyl]piperidine-2(R)-carboxylic acid derivatives of Formula I as described previously in Scheme C, step a.

Alternatively, the enantiomerically pure 2(S),3(R) saturated piperidine compounds of Formula I wherein $R_5$ is represented by hydrogen can be prepared as set forth in Scheme F by substituting L-aspartic acid for the D-aspartic acid (28).

Starting materials for use in Scheme F are readily available to one of ordinary skill in the art.

The following examples present typical syntheses as described in Scheme F. These examples are intended to be illustrative only and are not intended to limit the scope of the present invention in any way.

EXAMPLE 9

3(S)-(Phosphonoacetyl]piperidine-2(R)-carboxylic acid

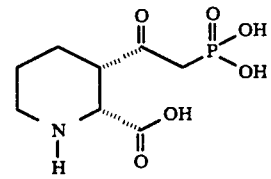

Step a: $\beta$-Methyl-D-aspartate hydrochloride

Cool methanol (525 mL) to −20° C. and place under an atmosphere of nitrogen. Add, by dropwise addition, thionyl chloride (80 mL). Add D-aspartic acid (100 g, 0.75 mol) in one portion and allow the reaction to warm to room temperature over approximately 1 hour. Stir for 50 minutes at room temperature and pour into anhydrous ethyl ether (1.5 L). Filter the resulting solid, dissolve partly in warm ethanol (500 mL) and filter again. Add the filtrated to ethyl ether (1.5 L) and filter the resulting solid. Dry to give the title compound (85.3 g, 62%).

$^1$H NMR (300 MHz, CDCl$_3$) ppm 4.22 (t, 1), 3.67 (s, 3), 2.96 (dd, 2).

Step b: $\alpha$-tert-Butyl-$\beta$-methyl-D-aspartate acetic acid

Suspend $\beta$-methyl-D-aspartate hydrochloride (40 g, 0.22 mol) in tert-butyl acetate (1.5 L) and add perchloric acid (20.7 mL of a 20% solution, 0.24 mol). Stir at room temperature under an atmosphere of argon for 3 hours. Pour into saturated sodium hydrogen carbonate and add solid sodium hydrogen carbonate until the mixture is basic. Add ethyl ether and separate the organic phase. Extract the aqueous phases with ethyl ether, combine the organic phases and dry (MgSO$_4$). Evaporate the solvent in vacuo to give the title compound as a clear oil (34 g).

$^1$H NMR (300 MHz, CDCl$_3$) ppm 5.64 (bs, 3), 3.78 (dd, 1), 3.76 (s, 3), 2.8 (m, 2), 2.04 (s, 3), 1.46 (s, 9).

Step c: $\alpha$-tert-Butyl-$\beta$-methyl-N-(3-chloropropyl)-D-aspartate

Mix $\alpha$-tert-butyl-$\beta$-methyl-D-aspartate acetic acid (36 g, 0.196 mol), 1-bromo-3-chloropropane (90 g), triethylamine (40 g) and acetonitrile (150 mL). Heat at 80° C. and stir for 16 hours. Evaporate the solvent to give a residue. Take up the residue in ethyl acetate (250 mL) and wash with brine (100 mL), saturated sodium hydrogen carbonate (100 mL) and brine (100 mL). Dry (Na$_2$SO$_4$) and evaporate the solvent in vacuo. Purify by silica gel chromatography (1:1 ethyl acetate/hexane) to give the title compound (32 g).

$^1$H NMR (90 MHz, CDCl$_3$) ppm 3.74 (s, 3), 3.6 (m, 2), 2.8 (m, 1), 2.65 (m, 2), 1.9 (m, 2), 1.5 (s, 9).

Step d:
α-tert-Butyl-β-methyl-N-(3-chloropropyl)-N-(9-phenylfluorenyl)-D-aspartate Add α-tert-butyl-β-methyl-N-(3-chloropropyl)-D-aspartate 24.8 g, 88.6 mmol) to anhydrous acetonitrile (150 mL) and place under a nitrogen atmosphere. Stir vigorously and add lead nitrate (24.8 g, 74.8 mmol). Simultaneously add, by dropwise addition over 5 hours, a solution of 9-phenylfluorenyl bromide (32 g, 99.6 mmol) in chloroform (100 mL) and a solution of diisopropylethylamine (20.4 mL, 117 mmol) in acetonitrile. Stir overnight at room temperature. Add methylene chloride (250 mL), filter and add methylene chloride (300 mL) to the filtrate. Wash with saturated sodium hydrogen carbonate (2×250 mL), brine (1×250 mL) and saturated sodium hydrogen carbonate (1×250 mL). Dry (Na$_2$SO$_4$) and evaporate to a residue. Purify by silica gel chromatography (10% hexane in methylene chloride) to give the title compound (26 g).

$^1$H NMR (300 MHz, CDCl$_3$) ppm 7.2–7.7 (m, 13), 3.79 (dd, 1), 3.6–3.4 (m, 2), 3.48 (s, 3), 3.2 (m, 1), 2185 (m, 1), 2.62 (dd, 1), 1.85–2.1 (m, 2), 1.8 (m, dd), 1.43 (s, 9).

Step e:
α-tert-Butyl-β-methyl-N-(3-iodopropyl)-N-(9-phenylfluorenyl)-D-aspartate Mix α-tert-butyl-β-methyl-N-(3-chloropropyl)-N-(9-phenylfluorenyl)-D-aspartate (26 g, 0.05 mol), sodium iodide (50 g) and anhydrous acetonitrile (250 mL). Place under a nitrogen atmosphere and stir at 65° C. for 16 hours. Cool and add methylene chloride (250 mL). Filter and evaporate the solvent to a residue. Take up the residue in methylene chloride (300 mL), wash with water (100 mL), 5% sodiumthiosulphate (100 mL), water (100 mL) and brine (100 mL). Dry (Na$_2$SO$_4$) and evaporate to a residue. Recrystallize (ethyl ether) to give the title compound (21.5 g).

$^1$H NMR (300 MHz, CDCl$_3$) ppm 7.2–7.8 (m, 13), 3.79 (dd, 1), 3.48 (s, 3), 2.95–3.2 (m, 3), 2.88 (m, 1), 1.8–2.3 (m, 2), 1.79 (dd, 1), 1.43 (s, 9).

Step f:
N-(9-Phenylfluorenyl)-piperidine-2(R)-tert-butyl-3(S)-methyl ester

Dissolve diisopropylamine (12 mL, 85.6 mmol) in anhydrous tetrahydrofuran, cool to −78° C. and place under an inert atmosphere. Add n-butyllithium (52 mL of a 1.6M solution in hexane, 83.2 mmol) and stir at −78° C. for 20 minutes. Add, by dropwise addition, a solution of α-tert-butyl-β-methyl-N-(3-iodopropyl)-N-(9-phenylfluorenyl)-D-aspartate (20 g, 32.7 mmol) in anhydrous tetrahydrofuran (50 mL). Stir at −78° C. for 1 hour, warm to −38° C. and stir for 3 hours. Cool to −78° C. and transfer via cannula to a −78° C. solution of diisopropyl phenol (30.8 g, 0.17 mol) in tetrahydrofuran (200 mL). Stir for 1 hour and add add acetic acid (5.2 mL). Warm to room temperature and quench with water (100 mL). Partition between methylene chloride (500 mL) and water (300 mL). Separate the organic phase, dry (Na$_2$SO$_4$) and evaporate to a residue. Purify by silica gel chromatography (10% hexane in methylene chloride) to give the title compound (13.8 g).

$^1$H NMR (CDCl$_3$) ppm 7.2–7.8 (m, 13), 3.82 (d, 1), 3.69 (td, 1), 3.55 (s, 3), 3.11 (m, 1), 2.91 (m, 1), 2.08 (m, 1), 1.6–1.9 (m, 2), 1.31 (m, 1), 1.03 (m, 9).

Step q:
N-(9-Phenylfluorenyl)-3(S)-[(diethoxyphosphinyl)acetyl]piperidine-2(R)-carboxylic acid, tert-butyl ester Dissolve diethyl methylphosphate (0.57 g) in anhydrous tetrahydrofuran (10 mL), cool to −78° C. and place under an argon atmosphere. Add, by dropwise addition, n-butyllithium (2.34 mL of a 1.6M solution). Stir for 20 minutes at −78° C. and add a solution of N-(9-phenylfluorenyl)-piperidine-2(R)-tert-butyl-3(S)-methyl ester (0.6 g, 1.24 mmol) in anhydrous tetrahydrofuran (10 mL). Stir for 2 hours at −78° C., quench with acetic acid (1 mL) and warm to room temperature. Pour into ethyl acetate (100 mL) and wash with brine (100 mL) and aqueous sodium hydrogen caronate (100 mL). Evaporate the a residue and purify by silica gel chromatography (ethyl acetate) to give the title compound (0.45 g).

$^1$H NMR (300 MHz, CDCl$_3$) ppm 7.2–7.8 (m, 13), 4.13 (m, 4), 3.79 (d, 1), 3.73 (m, 1), 3.23 (m, 1), 3.09 (m, 1), 3.03 (dd, 1).

Step h:
3(S)-(Phosphonoacetyl]piperidine-2(R)-carboxylic acid

Mix trifluoroacetic acid (30 mL) with acetonitrile (10 mL) and add, by dropwise addition, to an ice-cold solution of N-(9-phenylfluorenyl)-3(S)-[(diethoxyphosphinyl)acetyl]piperidine-2(R)-carboxylic acid, tert-butyl ester (3.5 g, 5.8 mmol) in acetonitrile (40 mL) and water (4 mL). Stir for 15 minutes, warm to room temperature and stir for an additional hour. Pour into saturated aqueous sodium hydrogen carbonate (500 mL) and extract into ethyl acetate (3×200 mL). Evaporate to a residue and take up the residue in acetonitrile (20 mL) and methylene chloride (20 mL). Place under a nitrogen atmosphere and add trimethylsilyl chloride (5 mL, 35 mmol). Stir overnight then add water. Stir for 15 minutes then blow to a residue with a stream of dry nitrogen. Take up the residue in water (100 mL) and wash with toluene (5×100 mL). Freeze dry to give a residue. Take up the residue in methanol (10 mL) and isopropanol (5 mL). Add propylene oxide (5 mL) and filter to give the title compound.

$^1$H NMR (300 MHz, D$_2$O) ppm 3.88 (d, 1), 3.73 (m, 1), 3.41 (m, 1), 3.14 (dd, 2), 3.01 (m, 1), 2.87 (m, 1), 1.98 (m, 1), 1.82 (m, 1), 1.55 (m, 1).

The following compounds can be prepared in a similar fashion to that described above in Example 9:

3(S)-(Phosphonoacetyl]piperidine-5-methyl-2(R)-carboxylic acid;

3(S)-(Phosphonoacetyl]piperidine-5-benzyl-2(R)-carboxylic acid.

An alternative synthetic procedure for preparing the enatiomerically pure 2(R), 3(R) saturated piperidine compounds of Formula I wherein R$_5$ is represented by hydrogen is set forth in Scheme G. In Scheme G, all substituents unless otherwise indicated are as previously defined.

Scheme G

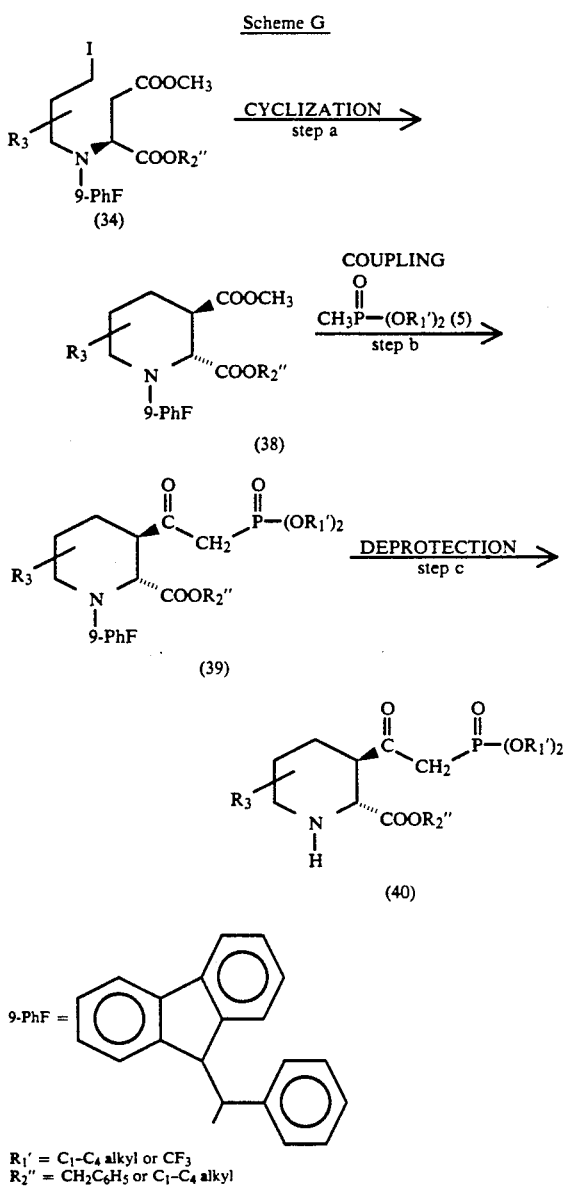

$R_1' = C_1-C_4$ alkyl or $CF_3$
$R_2'' = CH_2C_6H_5$ or $C_1-C_4$ alkyl

Scheme G provides an alternative synthetic procedure for preparing the enatiomerically pure 2(R), 3(R) saturated piperidine compounds of Formula I wherein $R_5$ is represented by hydrogen.

In step a, the appropriate α-$C_1-C_4$ alkyl or benzyl-β-methyl-N-(3-iodopropyl)-N-(9-phenylfluorenyl)-D-aspartate of structure (34) is cyclized to give the corresponding N-(9-phenylfluorenyl)-piperidine-2(R)-$C_1-C_4$ alkyl or benzyl ester-3(R)-methyl ester of structure (38) as described previously in Scheme F, step f.

In step b, the appropriate N-(9-phenylfluorenyl)-piperidine-2(R)-$C_1-C_4$ alkyl or benzyl ester-3(R)-methyl ester of structure (38) is coupled with the appropriate phosphonate ester of structure (5) to give the corresponding N-(9-phenylfluorenyl)-3(R)-[(dialkoxyphosphinyl)acetyl]piperidine-2(R)-carboxylic acid, benzyl or $C_1-C_4$ alkyl ester of structure (39) as described previously in Scheme A, step d.

In step c, the appropriate N-(9-phenylfluorenyl)-3(R)-[(dialkoxyphosphinyl)acetyl]piperidine-2(R)-carboxylic acid, benzyl or $C_1-C_4$ alkyl ester of structure (39) is deprotected to give the corresponding 3(R)-[(dialkoxyphosphinyl)acetyl]piperidine-2(R)-carboxylic acid, benzyl or $C_1-C_4$ alkyl ester of structure (40) as described previously in Scheme A, step f.

The appropriate 3(R)-[(dialkoxyphosphinyl)acetyl]-piperidine-2(R)-carboxylic acid, benzyl or $C_1-C_4$ alkyl ester of structure (40) can be further functionalized as described previously in Scheme A, steps $g_1$-i.

The appropriate 3-[(functionalized phosphinyl)acetyl]piperidine-2-carboxylic acid derivatives of Formula I prepared as described above in Scheme G may also be further functionalized into the corresponding 3(R)-[1-imino-2-phosponoethyl]piperidine-2(R)-carboxylic acid derivatives of Formula I as described previously in Scheme C, step a.

Alternatively, the enantiomerically pure 2(S),3(S) saturated piperidine compounds of Formula I wherein $R_5$ is represented by hydrogen can be prepared as set forth in Scheme G by substituting α-$C_1-C_4$ alkyl or benzyl-β-methyl-N-(3-iodopropyl)-N-(9-phenylfluorenyl)-L-aspartate for α-$C_1-C_4$ alkyl or benzyl-β-methyl-N-(3-iodopropyl)-N-(9-phenylfluorenyl)-D-aspartate of structure (34). The appropriate α-$C_1-C_4$ alkyl or benzyl-β-methyl-N-(3-iodopropyl)-N-(9-phenylfluorenyl)-L-aspartate can be prepared as set forth in Scheme F by substituting L-aspartic acid for the D-aspartic acid (28).

Starting materials for use in Scheme G are readily available to one of ordinary skill in the art.

The following examples present typical syntheses as described in Scheme G. These examples are intended to be illustrative only and are not intended to limit the scope of the present invention in any way.

EXAMPLE 10

3(R)-(Phosphonoacetyl]piperidine-2(R)-carboxylic acid, methyl ester

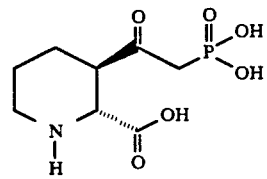

Step a:
N-(9-Phenylfluorenyl)-piperidine-2(R)-tert-butyl-3(R)-methyl ester

Dissolve diisopropylamine (0.6 mL, 4.3 mmol) in tetrahydrofuran (10 mL) and cool to 0° C. Add, by dropwise addition, n-butyllithium (2.7 mL of a 1.6M solution, 4.3 mmol). Stir for ½ hour, cool to −78° C. and add, by dropwise addition, a solution of α-tert-butyl-β-methyl-N-(3-iodopropyl)-N-(9-phenylfluorenyl)-D-aspartate (1 g, 1.6 mmol) in tetrahydrofuran (10 mL). Stir for 1 hour at −78° C. and then for 3 hours at −30° C. Transfer rapidly, via water heated cannula, to a −78° C. solution of acetic acid in tetrahydrofuran (10 mL). Allow to warm to room temperature overnight. Add ethyl acetate and wash with brine. Evaporate to a residue and purify by silica gel chromatography (50:50 to 75:25 methylene chloride/hexane) to give the title compound (0.35 g).

Step b:
N-(9-Phenylfluorenyl)-3(R)-[(diethoxyphosphinyl)acetyl]piperidine-2(R)-carboxylic acid, tert-butyl ester Dissolve diethyl methylphosphate (0.3 g) in anhydrous tetrahydrofuran, cool to −78° C. and place under an argon atmosphere. Add, by dropwise addition, n-butyllithium (1.16 mL of a 1.6M solution). Stir for ½ hour at −78° C. and add a solution of N-(9-phenylfluorenyl)-piperidine-2(R)-tert-butyl-3(R)-methyl ester (0.3 g, 0.62 mmol) in anhydrous tetrahydrofuran (10 mL). Allow to warm to −30° C. and stir for 3 hours, then cool to −78° C. and quench with acetic acid. Warm to room temperature, pour into ethyl ether (250 mL) and wash with brine (100 mL). Dry (Na$_2$SO$_4$) and evaporate to a residue. Purify by silica gel chromatography (ethyl acetate) to give the title compound (0.3 g).

$^1$H NMR (300 MHz, CDCl$_3$) ppm 7.15–7.75 (m, 13), 4.15 (m, 4), 3.79 (m, 1), 3.73 (m, 1), 3.05–3.2 (m, 3), 2.72 (m, 1), 1.75–2.05 (m, 3), 1.55 (m, 1), 1.35 (m, 7), 1.04 (s, 9).

Step c:
3(R)-(Phosphonoacetyl]piperidine-2(R)-carboxylic acid, methyl ester

Mix trifluoroacetic acid (30 mL) with acetonitrile (10 mL) and add, by dropwise addition, to an ice-cold solution of N-(9-phenylfluorenyl)-3(R)-[(diethoxyphosphinyl)acetyl]piperidine-2(R)-carboxylic acid, tert-butyl ester (3.5 g, 5.8 mmol) in acetonitrile (40 mL) and water (4 mL). Stir for 15 minutes, warm to room temperature and stir for an additional hour. Pour into saturated aqueous sodium hydrogen carbonate (500 mL) and extract into ethyl acetate (3×200 mL). Evaporate to a residue and take up the residue in acetonitrile (20 mL) and methylene chloride (20 mL). Place under a nitrogen atmosphere and add trimethylsilyl chloride (5 mL, 35 mmol). Stir overnight then add water. Stir for 15 minutes then blow to a residue with a stream of dry nitrogen. Take up the residue in water (100 mL) and wash with toluene (5×100 mL). Freeze dry to give a residue. Take up the residue in methanol (10 mL) and isopropanol (5 mL). Add propylene oxide (5 mL) and filter to give the title compound.

The 2(R),3(S) saturated piperidine compounds of Formula I wherein R$_5$ is represented by linear C$_1$–C$_4$ alkyl, or phenylalkyl can be prepared by techniques and procedures well known and appreciated by one of ordinary skill in the art. A general synthetic scheme for preparing these compounds is set forth in Scheme H. In Scheme H all substituents unless otherwise indicated are as previously defined.

Scheme H

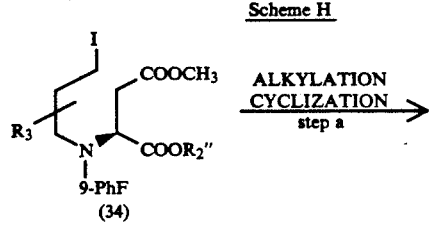

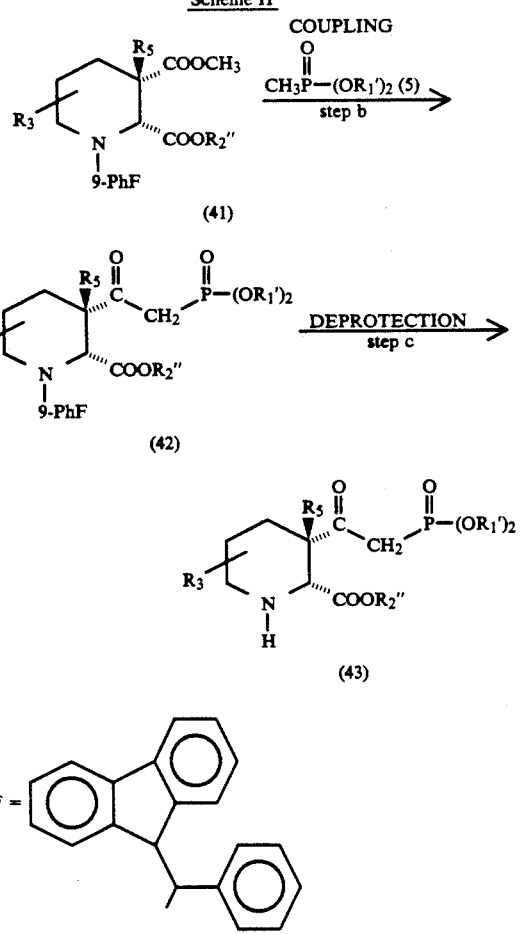

$R_1' = C_1-C_4$ alkyl or $CF_3$
$R_2'' = CH_2C_6H_5$ or $C_1-C_4$ alkyl

Scheme H provides a general synthetic procedure for preparing the 2(R),3(S) saturated piperidine compounds of Formula I wherein R$_5$ is represented by linear C$_1$–C$_4$ alkyl, or phenylalkyl.

In step a, the appropriate α-C$_1$–C$_4$ alkyl or benzyl-β-methyl-N-(3-iodopropyl)-N-(9-phenylfluorenyl)-D-aspartate of structure (34) is alkylatively cyclized with the appropriate alkylating agent of the formula R$_5$-Hal, wherein Hal is Br or I, to give the corresponding N-(9-phenylfluorenyl)-piperidine-2(R)-C$_1$–C$_4$ alkyl or benzyl ester-3(R)-alkyl-3(S)-methyl ester of structure (41). The appropriate alkylating agent of the formula R$_5$-Hal, wherein Hal is Br or I is one in which R$_5$ is the same as is desired in the final product.

For example, the appropriate α-C$_1$–C$_4$ alkyl or benzyl-β-methyl-N-(3-iodopropyl)-N-(9-phenylfluorenyl)-D-asparate of structure (34) is contacted with an appropriate base such as lithium diisopropylamine. The reactants are typically contacted in a suitable organic solvent such as tetrahydrofuran. The reactants are typically stirred together for a period of time ranging from 2–20 hours and at a temperature range of from −78° C. to −20° C. The N-(9-phenylfluorenyl)-piperidine-2(S)-C$_1$–C$_4$ alkyl or benzyl ester-3(R)-alkyl-3(S)-methyl ester of structure (41) is recovered from the reaction zone by a low-temperature quench into an appropriate alkylating agent of the formula R$_5$-Hal, followed by acidification and extraction as is known in the art. It may be purified by silica gel chromatography.

In step b, the appropriate N-(9-phenylfluorenyl)-piperidine-2(R)-C₁-C₄ alkyl or benzyl ester-3(R)-alkyl-3(S)-methyl ester of structure (41) is coupled with the appropriate phosphonate ester of structure (5) to give the corresponding N-(9-phenylfluorenyl)-3(S)-[(dialkoxyphosphinyl)acetyl]piperidine-3(R)-alkyl-2(R)-carboxylic acid, benzyl or C₁-C₄ alkyl ester of structure (42) as described previously in Scheme A, step d.

In step c, the appropriate N-(9-phenylfluorenyl)-3(S)-[(dialkoxyphosphinyl)acetyl]piperidine-3(R)-alkyl-2(R)-carboxylic acid, benzyl or C₁-C₄ alkyl ester of structure (42) is deprotected to give the corresponding 3(S)-[(dialkoxyphosphinyl)acetyl]piperidine-3(R)-alkyl-2(R)-carboxylic acid, benzyl or C₁-C₄ alkyl ester of structure (43).

The appropriate 3(S)-[(dialkoxyphosphinyl)acetyl]-piperidine-3(R)-alkyl-2(R)-carboxylic acid, benzyl or C₁-C₄ alkyl ester of structure (43) can be further functionalized as described previously in Scheme A, steps g1-i.

The appropriate 3(S)-[(functionalized phosphinyl)acetyl]piperidine-3(R)-alkyl-2(R)-carboxylic acid derivatives of Formula I prepared as described above in Scheme H may also be further functionalized into the corresponding 3(S)-[1-imino-2-phosponoethyl]piperidine-3(R)-alkyl-2(R)-carboxylic acid derivatives of Formula I as described previously in Scheme C, step a.

Alternatively, the enantiomerically pure 2(S),3(R) saturated piperidine compounds of Formula I wherein R₅ is represented by linear C₁-C₄ alkyl, or phenylalkyl can be prepared as set forth in Scheme H by substituting the appropriate N-(9-phenylfluorenyl)piperidine-2(S)-C₁-C₄ alkyl or benzyl ester-3(R)-methyl ester for the appropriate N-(9-phenylfluorenyl)piperidine-2(R)-C₁-C₄ alkyl or benzyl ester-3(S)-methyl ester of structure (35). The appropriate N-(9-phenylfluorenyl)piperidine-2(S)-C₁-C₄ alkyl or benzyl ester-3(R)-methyl ester can be prepared as set forth in Scheme F by substituting L-aspartic acid for the D-aspartic acid (28).

Starting materials for use in Scheme H are readily available to one of ordinary skill in the art.

The following examples present typical syntheses as described in Scheme H. These examples are intended to be illustrative only and are not intended to limit the scope of the present invention in any way.

EXAMPLE 11

3(S)-(Phosphonoacetyl]piperidine-3(R)-methyl-2(R)-carboxylic acid

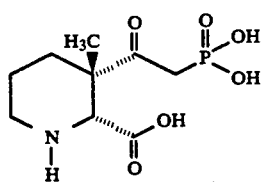

Step A:
N-(9-Phenylfluorenyl)piperidine-3(R)-methyl-2(R)-tert-butyl ester-3(S)-methyl ester Dissolve diisopropylamine (0.73 mL) in anhydrous tetrahydrofuran (10 mL), cool to 0° C. and place under an inert atmosphere. Add, by dropwise addition, n-butyllithium (3.11 mL of a 1.6M solution in hexane) and stir for 15 minutes at 0° C. then at −78° C. for 15 minutes. Add, by dropwise addition, a solution of α-tert-butyl-β-methyl-N-(3-iodopropyl)-N-(9-phenylfluorenyl)-D-aspartate (1.22 g) in anhydrous tetrahydrofuran (10 mL). Stir for 1 hour at −78° C. then at −38° C. for 3 hours. Cool to −78° C. and add via cannula to a solution of iodomethane (3 mL) in tetrahydrofuran (10 mL). Stir at −78° C. for 3 hours, quench with acetic acid and warm to room temperature. Evaporate to a residue and purify by silica gel chromatography (methylene chloride) to give impure title compound.

Dissolve diisopropylamine (0.35 mL, 2.5 mmol) in anhydrous tetrahydrofuran, cool to 0° C. and place under an inert atmosphere. Add, by dropwise addition, n-butyllithium (1.4 mL of a 1.6M solution in hexane, 2.5 mmol) and stir for ½ hour at 0° C. Cool to −78° C. and add hexamethylphosphoramide (0.43 mL, 2.5 mmol) followed by a solution of N-(9-phenylfluorenyl)piperidine-2(S)-tert-butyl ester-3(S)-methyl ester (0.8 g, 1.7 mmol) in anhydrous tetrahydrofuran (5 mL). Stir for ½ hour and add iodomethane (0.42 mL, 6.8 mmol). Stir at −78° C. overnight, quench with actic acid and warm to room temperature. Evaporate to a residue and purify by silica gel chromatography (80:20/methylene chloride/hexane) to give the title compound (0.56 g).

¹H NMR (300 MHz, CDCl₃) ppm 7.18–7.75 (m, 13), 3.93 (s, 1), 3.88 (s, 3), 3.82 (m, 1), 3.08 (m, 1), 2.59 (m, 1), 2.14 (m, 1), 1.98 (m, 1), 1.78 (m, 1), 1.62 (m, 1), 1.08 (s, 9).

Step b:
N-(9-Phenylfluorenyl)-3(S)-[(diethoxyphosphinyl)acetyl]piperidine-3(R)-methyl-2(R)-carboxylic acid, tert-butyl ester Dissolve diethyl methylphosphonate (1.14 g, 7.5 mmol) in anhydrous tetrahydrofuran (10 mL), cool to −78° C. and place under an inert atmosphere. Add n-butyllithium (4.68 mL of a 1.6M solution in hexane, 7.5 mmol) and stir for 20 minutes. Add, by dropwise addition, a solution of N-(9-phenylfluorenyl)piperidine-3(R)-methyl-2(R)-tert-butyl ester-3(S)-methyl ester (0.55 g, 1.1 mmol) in anhydrous tetrahydrofuran (10 mL). Stir for 4 hours at −48° C. and add acetic acid (2 mL). Warm to room temperature, evaporate to a residue and purify by silica gel chromatography (ethyl acetate) to give the title compound (0.33 g).

¹H NMR (300 MHz, CDCl₃) ppm 7.18–8.75 (m, 13), 4.10 (m, 4), 3.54 (m, 1), 3.51 (s, 1), 3.15 (m, 1), 2.99 (m, 2), 2.48 (m, 1), 1.98 (m, 1), 1.29 (m, 6), 0.92 (s, 9).

Step c:
3(S)-(Phosphonoacetyl]piperidine-3(R)-methyl-2(R)-carboxylic acid

Dissolve N-(9-phenylfluorenyl)-3(S)-[(diethoxyphosphinyl)acetyl]piperidine-3(R)-methyl-2(R)-carboxylic acid, tert-butyl ester (0.35 g) in acetonitrile and cool to 0° C. Stir vigorously and add, by dropwise addition, a solution of trifluoroacetic acid (20 mL) in water (2 mL). Stir for 15 minutes, warm to room temperature and stir for 3 hours. Evaporate the a solid residue, take up in water (100 mL) and wash with toluene (100 mL). Freeze dry the aqueous phase to give a white solid. Take up the white solid in acetonitrile (10 mL) and methylene chloride (10 mL). Pass a gentle stream of nitrogen through the solution and add trimethylsilyliodide (2 mL). Stir for 6 hours, quench with water and wash with toluene (5×100 mL). Freeze dry the aqueous phase and dissolve the resulting yellow solid in methanol (5 mL) and isopropanol (2.5 mL). Add propylene oxide (2.0 mL) and stir for 2 hours. Filter to give the title compound.

$^1$H NMR (300 MHz, D$_2$O) ppm, 3.69 (s, 1), 3.32 (m, 1), 2.9 (m, 1), 2.28 (m, 1), 1.4–1.8 (m, 3), 1.53 (s, 3).

The following compounds can be prepared in a similar fashion to that described above in Example 11:

3(S)-(Phosphonoacetyl]piperidine-5-benzyl-3(R)-methyl-2(R)-carboxylic acid.

The 2(R)-3-unsaturated piperidine compounds of Formula I can be prepared by techniques and procedures well known and appreciated by one of ordinary skill in the art. A general synthetic procedure for preparing these compounds is set forth in Scheme I. In Scheme I all substituents unless otherwise indicated are as previously defined.

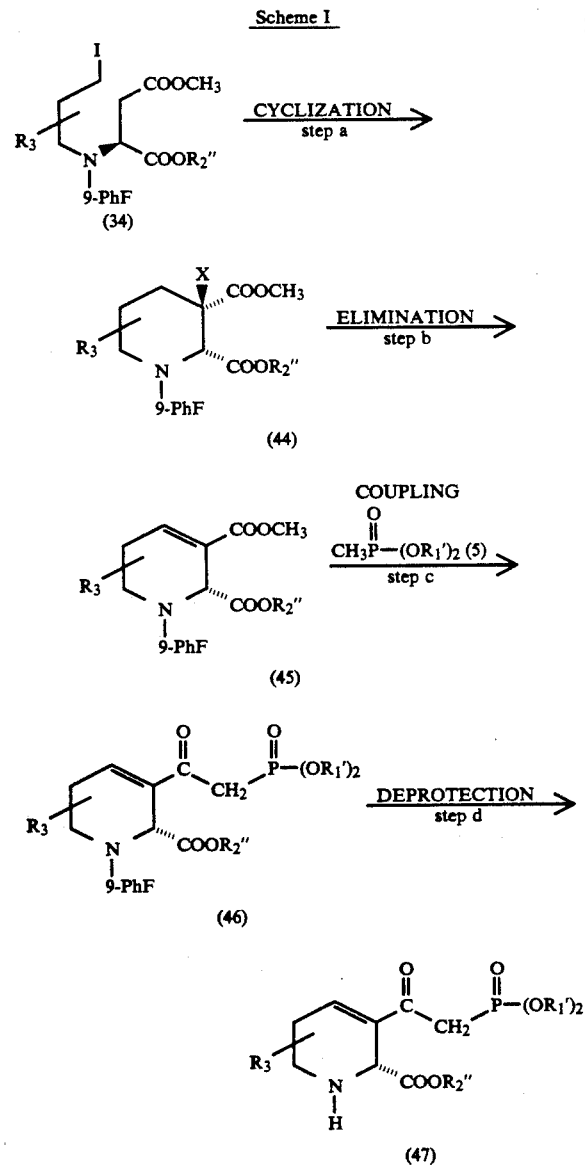

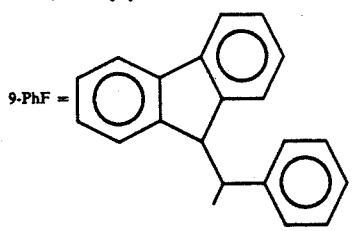

$X = I, -SeC_6H_5$

9-PhF =

$R_1' = C_1-C_4$ alkyl or $CF_3$
$R_2'' = CH_2C_6H_5$ or $C_1-C_4$ alkyl

Scheme I provides a general synthetic procedure for preparing the 2(R)-3-unsaturated piperidine compounds of Formula I.

In step a, the appropriate α-C$_1$–C$_4$ alkyl or benzyl-β-methyl-N-(3-iodopropyl)-N-(9-phenylfluorenyl)-D-aspartate of structure (34) is cyclized and either iodinated or selenated to give the corresponding N-(9-phenylfluorenyl)piperidine-3(R)-iodo-2(R)-C$_1$–C$_4$ alkyl or benzyl ester-3(S)-methyl ester of structure (44) or N-(9-phenylfluorenyl)piperidine-3(R)-phenylselenyl-2(R)-C$_1$–C$_4$ alkyl or benzyl ester-3(S)-methyl ester of structure (44).

For example, the appropriate α-C$_1$–C$_4$ alkyl or benzyl-β-methyl-N-(3-iodopropyl)-N-(9-phenylfluorenyl)-D-aspartate of structure (34) is contacted with an appropriate base such as lithium diisopropylamine. The reactants are typically contacted in a suitable organic solvent such as tetrahydrofuran. The reactants are typically stirred together for a period of time ranging from 2–20 hours and at a temperature range of from −78° C. to −20° C. The N-(9-phenylfluorenyl)piperidine-3(R)-iodo-2(R)-C$_1$–C$_4$ alkyl or benzyl ester-3(S)-methyl ester of structure (44) or N-(9-phenylfluorenyl)piperidine-3(R)-phenylselenyl-2(R)-C$_1$–C$_4$ alkyl or benzyl ester-3(S)-methyl ester of structure (44) is recovered from the reaction zone by a low-temperature quench into iodine or diphenyldiselenide, followed by acidification and extraction as is known in the art. It may be purified by silica gel chromatography.

When N-(9-phenylfluorenyl)piperidine-3(R)-phenylselenyl-2(R)-C$_1$–C$_4$ alkyl or benzyl ester-3(S)-methyl ester of structure (44) is prepared in step a, the selenyl functionality must be subsequently oxidized by techniques well known in the art to give the corresponding N-(9-phenylfluorenyl)piperidine-3(R)-phenylselenoxyl-2(R)-C$_1$–C$_4$ alkyl or benzyl ester-3(S)-methyl ester before continuing with step b.

In step b, the appropriate N-(9-phenylfluorenyl)-piperidine-3(R)-iodo-2(R)-C$_1$–C$_4$ alkyl or benzyl ester-3(S)-methyl ester of structure (44) or N-(9-phenylfluorenyl)piperidine-3(R)-phenylselenoxyl-2(R)-C$_1$–C$_4$ alkyl or benzyl ester-3(S)-methyl ester is eliminated to give the corresponding N-(9-phenylfluorenyl)-3-piperidene-2(R)-C$_1$–C$_4$ alkyl or benzyl ester-3-methyl ester of structure (45).

For example, the appropriate N-(9-phenylfluorenyl)-piperidine-3(R)-iodo-2(R)-C$_1$–C$_4$ alkyl or benzyl ester-3(S)-methyl ester of structure (44) or N-(9-phenylfluorenyl)piperidine-3(R)-phenylselenoxyl-2(R)-C$_1$–C$_4$ alkyl or benzyl ester-3(S)-methyl ester is contacted with a molar excess of a strong base, such as 1,8-diazabicyclo[5.4.0]undec-7-ene (DBU). The reactants are typically contacted in a suitable organic solvent such as benzene. The reactants are typically stirred together for a period of time ranging from 2-24 hours and at a temperature range of from room temperature to 80° C. The N-(9-phenylfluorenyl)-3-piperidene-2(R)-$C_1$-$C_4$ alkyl or benzyl ester-3-methyl ester of structure (45) is recovered from the reaction zone by extractive methods as is known in the art. It may be purified by silica gel chromatography.

In step c, the appropriate N-(9-phenylfluorenyl)-3-piperidene-2(R)-$C_1$-$C_4$ alkyl or benzyl ester-3-methyl ester of structure (45) is coupled with the appropriate phosphonate ester of structure (5) to give the corresponding N-(9-phenylfluorenyl)-3-[(dialkoxyphosphinyl)acetyl]-3-piperidene-2(R)-carboxylic acid, benzyl or $C_1$-$C_4$ alkyl ester of structure (46) as described previously in Scheme A, step d.

In step d, the appropriate N-(9-phenylfluorenyl)-3-[(dialkoxyphosphinyl)acetyl]-3-piperidene-2(R)-carboxylic acid, benzyl or $C_1$-$C_4$ alkyl ester of structure (46) is deprotected to give the corresponding 3-[(dialkoxyphosphinyl)acetyl]-3-piperidene-2(R)-carboxylic acid, benzyl or $C_1$-$C_4$ alkyl ester of structure (47) as described previously in Scheme A, step f.

The appropriate 3-[(dialkoxyphosphinyl)acetyl]-3-piperidene-2(R)-carboxylic acid, benzyl or $C_1$-$C_4$ alkyl ester of structure (47) can be further functionalized as described previously in Scheme A, steps $g_1$-i.

The appropriate 3-[(functionalized phosphinyl)acetyl]-3-piperidene-2(R)-carboxylic acid derivatives of Formula I prepared as described above in Scheme H may also be further functionalized into the corresponding 3-[1-imino-2-phosponoethyl]-3-piperidene-2(R)-carboxylic acid derivatives of Formula I as described previously in Scheme C, step a.

Alternatively, the enantiomerically pure 2(S)-3-unsaturated piperidine compounds of Formula I can be prepared as set forth in Scheme I by substituting the appropriate α-$C_1$-$C_4$ alkyl or benzyl-β-methyl-N-(3-iodopropyl)-N-(9-phenylfluorenyl)-L-aspartate for the appropriate α-$C_1$-$C_4$ alkyl or benzyl-β-methyl-N-(3-iodopropyl)-N-(9-phenylfluorenyl)-D-aspartate of structure (34). The appropriate α-$C_1$-$C_4$ alkyl or benzyl-β-methyl-N-(3-iodopropyl)-N-(9-phenylfluorenyl)-L-aspartate can be prepared as set forth in Scheme F by substituting L-aspartic acid for the D-aspartic acid (28).

Starting materials for use in Scheme I are readily available to one of ordinary skill in the art.

The following examples present typical syntheses as described in Scheme I. These examples are intended to be illustrative only and are not intended to limit the scope of the present invention in any way.

EXAMPLE 12

3-(Phosphonoacetyl]-3-piperidene-2(R)-carboxylic acid

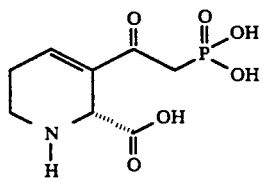

Step a:
N-(9-Phenylfluorenyl)piperidine-3(R)-iodo-2(R)-tert-butyl ester-3-(S)-methyl ester Dissolve diisopropylamine (2.4 mL, 17.12 mmol) in anhydrous tetrahydrofuran (80 mL), cool to 0–5° C. and place under an inert atmosphere. Add n-butyllithium (10.5 mL of a 1.6M solution in hexane, 16.8 mmol) and cool to −70°-75° C. Add a solution of α-tert-butyl-β-methyl-N-(3-iodopropyl)-N-(9-phenylfluorenyl)-D-aspartate (4.0 g, 6.54 mmol) in tetrahydrofuran (10 mL). Stir at −78° C. for 1 hour, then warm to −35° C. and stir for 3–4 hours to give the enolate.

Dissolve iodine (2.5 g, 9.85 mmol) in tetrahydrofuran (30 mL) and cool to −78° C. Add the −40° C. solution of the enolate and stir overnight, slowly warming to room temperature. Add phosphoric acid (20 mL of a 0.5M solution) and extract into ethyl ether (3×20 mL). Combine the organic phases and wash with saturated sodium thiosulfate (10 mL) and saturated sodium hydrogen carbonate (20 mL). Dry ($MgSO_4$/$Na_2SO_4$) and evaporate the solvent in vacuo to give the title compound (3.99 g).

$^1$H NMR (300MHz, $CDCl_3$) ppm 7.1–1.9 (m, 13), 4.01 (s, 1), 3.75 (m, 1), 3.65 (s, 3), 3.28 (m, 1), 3.18 (m, 1), 2.2–2.4 (m, 1), 1.8 (m, 1), 1.3 (m, 1), 0.9 (s, 9).

Step b:
N-(9-Phenylfluorenyl)-3-piperidene-2(R)-tert-butyl ester-3-methyl ester Mix N-(9-phenylfluorenyl)piperidine-3(R)-iodo-2(R)-tert-butyl ester-3(S)-methyl ester (3.99 g, 6.55 mmol), 1,8-diazabicyclo[5.4.0]undec-7-ene (2.9 mL, 19.62 mmol) and benzene (8.5 mL). Heat to 65° C. fo several hours. Add phosphoric acid (50 mL of a 0.5M solution) and extract into ethyl ether (4×20 mL). Dry ($MgSO_4$/$Na_2SO_4$), evaporate the solvent in vacuo and purify by silica gel chromatography (30/70 ethyl ether/hexane) to give the title compound.

$^1$H NMR (300 MHz, $CDCl_3$) ppm 7.15–7.75 (m, 13), 6.98 (m, 1), 4.51 (s, 1), 3.68 (s, 3), 3.38 (m, 1), 3.05 (m, 1), 1.89 (m, 2), 1.2 (s, 9).

Step c:
N-(9-phenylfluorenyl)-3-[(diethoxyphosphinyl)acetyl]-3-piperidene-2(R)-carboxylic acid, tert-butyl ester Dissolve diethyl methylphosphonate (1.14 g, 7.5 mmol) in anhydrous tetrahydrofuran (10 mL), cool to −78° C. and place under an inert atmosphere. Add n-butyllithium (4.68 mL of a 1.6M solution in hexane, 7.5 mmol) and stir for 20 minutes. Add, by dropwise addition, a solution of N-(9-phenylfluorenyl)-3-piperidene-2(R)-tert-butyl ester-3-methyl ester (545 mg, 1.1 mmol) in anhydrous tetrahydrofuran (10 mL). Stir for 4 hours at −48° C. and add acetic acid (2 mL). Warm to room temperature, evaporate to a residue and purify by silica gel chromatography (ethyl acetate) to give the title compound.

Step d:
3-(Phosphonoacetyl]-3-piperidene-2(R)-carboxylic acid

Dissolve N-(9-phenylfluorenyl)-3-[(diethoxyphosphinyl)acetyl]-3-piperidene-2(R)-carboxylic acid, tert-butyl ester (0.35 g) in acetonitrile and cool to 0° C. Stir vigorously and add, by dropwise addition, a solution of trifluoroacetic acid (20 mL) in water (2 mL). Stir for 15 minutes, warm to room temperature and stir for 3 hours. Evaporate the a solid residue, take up in water (100 mL)

and wash with toluene (100 mL). Freeze dry the aqueous phase to give a residue. Take up the residue in acetonitrile (10 mL) and methylene chloride (10 mL). Pass a gentle stream of nitrogen through the solution and add trimethylsilyliodide (2 mL). Stir for 6 hours, quench with water and wash with toluene (5×100 mL). Freeze dry the aqueous phase and dissolve the resulting residue in methanol (5 mL) and isopropanol (2.5 mL). Add propylene oxide (2.0 mL) and stir for 2 hours. Filter to give the title compound.

The following compound can be prepared in a similar fashion to that described above in Example 12:
3-(Phosphonoacetyl]-3-piperidene-5-methyl-2(R)-carboxylic acid.

The 2(R), 3(S)-4-unsaturated piperidine compounds of Formula I can be prepared by techniques and procedures well known and appreciated by one of ordinary skill in the art. A general synthetic procedure for preparing these compounds is set forth in Scheme J. In Scheme J all substituents unless otherwise indicated are as previously defined.

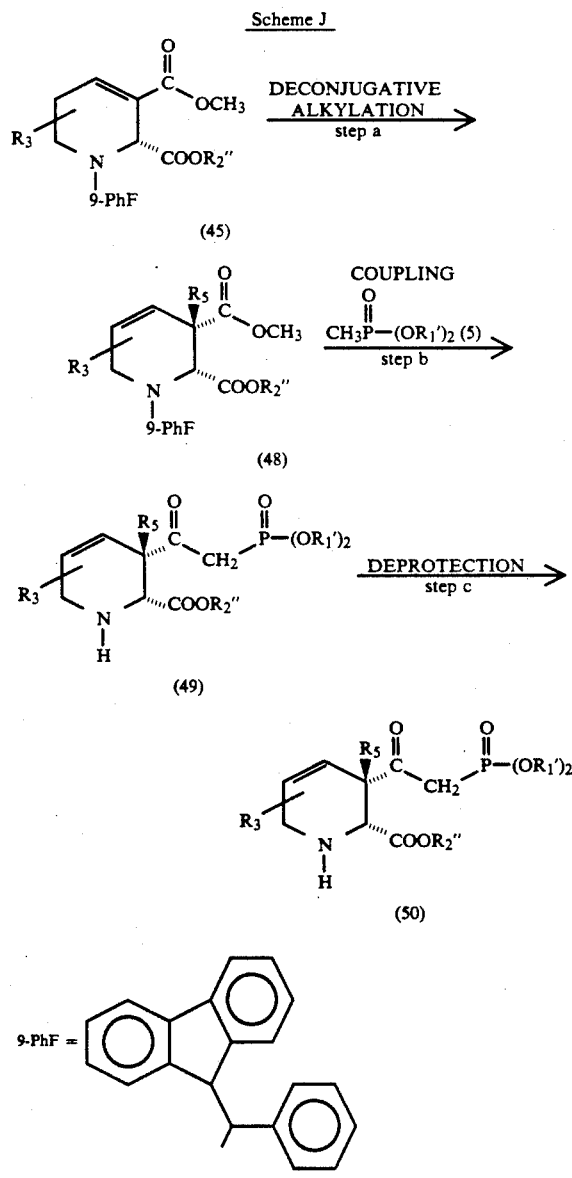

Scheme J provides a general synthetic scheme for preparing the 2(S), 3(S)-4-unsaturated piperidine compounds of Formula I.

In step a, the appropriate N-(9-phenylfluorenyl)-3-piperidene-2(R)-$C_1$-$C_4$ alkyl or benzyl ester-3-methyl ester of structure (45) undergoes a deconjucative alkylation to give the corresponding N-(9-phenylfluorenyl)-4-piperidene-2(R)-$C_1$-$C_4$ alkyl or benzyl ester-3-methyl ester of structure (48).

For example, the appropriate N-(9-phenylfluorenyl) 3-piperidene-2(R)-$C_1$-$C_4$ alkyl or benzyl ester-3-methyl ester of structure (45) is contacted with a strong base, such as n-butyllithium. The reactants are typically contacted in a suitable organic solvent such as tetrahydrofuran. The reactants are typically stirred together for a period of time ranging from 1–10 hours and at a temperature range of from $-78°$ C. to $-20°$ C. The N-(9-phenylfluorenyl)-4-piperidene-2(R)-$C_1$-$C_4$ alkyl or benzyl ester-3-methyl ester of structure (48) is recovered from the reaction zone by a low-temperature quench into an appropriate alkylating agent of the formula $R_5$-Hal or a proton source such as diisopropyl phenol, followed by acidification and extraction as is known in the art. It may be purified by silica gel chromatography.

In step b, the appropriate N-(9-phenylfluorenyl)-4-piperidene-2(R)-$C_1$-$C_4$ alkyl or benzyl ester-3-methyl ester of structure (48) is coupled with the appropriate phosphonate ester of structure (5) to give the corresponding N-(9-phenylfluorenyl)-3(S)-[(dialkoxyphosphinyl)acetyl]-4-piperidene-2(R)-carboxylic acid, benzyl or $C_1$-$C_4$ alkyl ester of structure (49) as described previously in Scheme A, step d.

In step c, the appropriate N-(9-phenylfluorenyl)-3(S)-[(dialkoxyphosphinyl)acetyl]-4-piperidene-2(R)-carboxylic acid, benzyl or $C_1$-$C_4$ alkyl ester of structure (49) is deprotected to give the corresponding 3(S)-[(dialkoxyphosphinyl)acetyl]-4-piperidene-2(R)-carboxylic acid, benzyl or $C_1$-$C_4$ alkyl ester of structure (50) as described previously in Scheme A, step f.

The appropriate 3(S)-[(dialkoxyphosphinyl)acetyl]-4-piperidene-2(R)-carboxylic acid, benzyl or $C_1$-$C_4$ alkyl ester of structure (50) can be further functionalized as described previously in Scheme A, steps $g_1$-i.

The appropriate 3(S)-[(functionalized phosphinyl)acetyl]-4-piperidene-2(R)-carboxylic acid derivatives of Formula I prepared as described above in Scheme J may also be further functionalized into the corresponding 3(S)-[1-imino-2-phosponoethyl]-4-piperidene-2(R)-carboxylic acid derivatives of Formula I as described previously in Scheme C, step a.

Alternatively, the enantiomerically pure the 2(S), 3(R)-4-unsaturated piperidine compounds of Formula I can be prepared as set forth in Scheme I by substituting the appropriate N-(9-phenylfluorenyl)-3-piperidene-2(S)-$C_1$-$C_4$ alkyl or benzyl ester-3-methyl ester for the appropriate N-(9-phenylfluorenyl)-3-piperidene-2(R)-$C_1$-$C_4$ alkyl or benzyl ester-3-methyl ester of structure (45). The appropriate N-(9-phenylfluorenyl)-3-piperidene-2(S)-$C_1$-$C_4$ alkyl or benzyl ester-3-methyl ester can be prepared as set forth in Scheme I by Substituting the appropriate $\alpha$-$C_1$-$C_4$ alkyl or benzyl-$\beta$-methyl-N-(3-iodopropyl)-N-(9-phenylfluorenyl)-L-aspartate for the appropriate $\alpha$-$C_1$-$C_4$ alkyl or benzyl-$\beta$-methyl-N-(3-iodopropyl)-N-(9-phenylfluorenyl)-L-aspartate of structure (34). The appropriate $\alpha$-$C_1$-$C_4$ alkyl or benzyl-$\beta$-methyl-N-(3-iodopropyl)-N-(9-phenylfluorenyl)-L-aspartate can be prepared as set forth in Scheme F by substituting L-aspartic acid for the D-aspartic acid (28).

In addition, the enantiomerically pure 2(R), 3(R)-4-unsaturated piperidine compounds of Formula I can be prepared as set forth in Scheme I by substituting the appropriate N-(benzyloxycarbonyl)-3-piperidene-2(R)-$C_1$-$C_4$ alkyl or benzyl ester-3-methyl ester for the appropriate N-(9-phenylfluorenyl)-3-piperidene-2(R)-$C_1$-$C_4$ alkyl or benzyl ester-3-methyl ester of structure (45) followed by an HPLC separation as set forth in Scheme B.

Alternatively, the enantiomerically pure 2(S), 3(S)-4-unsaturated piperidine compounds of Formula I can be prepared as set forth in Scheme I by substituting the appropriate N-(benzyloxycarbonyl)-3-piperidene-2(S)-$C_1$-$C_4$ alkyl or benzyl ester-3-methyl ester for the appropriate N-(9-phenylfluorenyl)-3-piperidene-2(S)-$C_1$-$C_4$ alkyl or benzyl ester-3-methyl ester of structure (45) followed by an HPLC separation as set forth in Scheme B. The appropriate N-(benzyloxycarbonyl)-3-piperidene-2(S)-$C_1$-$C_4$ alkyl or benzyl ester-3-methyl ester can be prepared as set forth in Scheme I by substituting the appropriate α-$C_1$-$C_4$ alkyl or benzyl-β-methyl-N-(3-iodopropyl)-N-(9-phenylfluorenyl)-L-aspartate for the appropriate α-$C_1$-$C_4$ alkyl or benzyl-β-methyl-N-(3-iodopropyl)-N-(9-phenylfluorenyl)-L-aspartate of structure (34). The appropriate α-$C_1$-$C_4$ alkyl or benzyl-β-methyl-N-(3-iodopropyl)-N-(9-phenylfluorenyl)-L-aspartate can be prepared as set forth in Scheme F by substituting L-aspartic acid for the D-aspartic acid (28).

Starting materials for use in Scheme J are readily available to one of ordinary skill in the art.

The following examples present typical syntheses as described in Scheme J. These examples are intended to be illustrative only and are not intended to limit the scope of the present invention in any way.

EXAMPLE 13

3(S)-(Phosphonoacetyl]-4-piperidene-2(R)-carboxylic acid

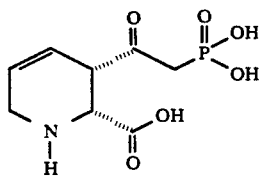

Step a: N-(9-Phenylfluorenyl) 4-piperidene-2(R)-carboxylic acid, tert-butyl ester Dissolve diisopropylamine (12 mL, 85.6 mmol) in anhydrous tetrahydrofuran, cool to −78° C. and place under an inert atmosphere. Add n-butyllithium (52 mL of a 1.6M solution in hexane, 83.2 mmol) and stir at −78° C. for 20 minutes. Add hexamethylphosphoramide and add, by dropwise addition, a solution of N-(9-phenylfluorenyl)-3-piperidene-2(R)-tert-butyl ester-3-methyl ester (16.2 g, 32.7 mmol) in anhydrous tetrahydrofuran (50 mL). Stir at −78° C. for 1 hour, warm to −48° C. and stir for 3 hours. Cool to −78° C. and transfer via cannula to a −78° C. solution of diisopropyl phenol (30.8 g, 0.17 mol) in tetrahydrofuran (200 mL). Stir for 1 hour and add add acetic acid (5.2 mL). Warm to room temperature and quench with water (100 mL). Partition between methylene chloride (500 mL) and water (300 mL). Separate the organic phase, dry ($Na_2SO_4$) and evaporate to a residue. Purify by silica gel chromatography to give the title compound.

Step b: N-(9-Phenylfluorenyl)-3(S)-[(diethoxyphosphinyl)acetyl]-4-piperidene-2(R)-carboxylic acid, tert-butyl ester Dissolve diethyl methylphosponate (1.14 g, 7.5 mmol) in anhydrous tetrahydrofuran (10 mL), cool to −78° C. and place under an inert atmosphere. Add n-butyllithium (4.68 mL of a 1.6M solution in hexane, 7.5 mmol) and stir for 20 minutes. Add, by dropwise addition, a solution of N-(9-phenylfluorenyl)-4-piperidene-2(R)-carboxylic acid, tert-butyl ester (529 mg, 1.1 mmol) in anhydrous tetrahydrofuran (10 mL). Stir for 4 hours at −48° C. and add acetic acid (2 mL). Warm to room temperature, evaporate to a residue and purify by silica gel chromatography (ethyl acetate) to give the title compound.

Step c: 3(S)-(Phosphonoacetyl]-4-piperidene-2(R)-carboxylic acid

Dissolve N-(9-phenylfluorenyl)-3(S)-[(diethoxyphosphinyl)acetyl]-4-piperidene-2(R)-carboxylic acid, tert-butyl ester (0.35 g) in acetonitrile and cool to 0° C. Stir vigorously and add, by dropwise addition, a solution of trifluoroacetic acid (20 mL) in water (2 mL). Stir for 15 minutes, warm to room temperature and stir for 3 hours. Evaporate to a solid residue, take up in water (100 mL) and wash with toluene (100 mL). Freeze dry the aqueous phase to give a residue. Take up the residue in acetonitrile (10 mL) and methylene chloride (10 mL). Pass a gentle stream of nitrogen through the solution and add trimethylsilyliodide (2 mL). Stir for 6 hours, quench with water and wash with toluene (5 × 100 mL). Freeze dry the aqueous phase and dissolve the resulting residue in methanol (5 mL) and isopropanol (2.5 mL). Add propylene oxide (2.0 mL) and stir for 2 hours. Filter to give the title compound.

EXAMPLE 14

3(S)-(Phosphonoacetyl]-3(R)-methyl-4-piperidene-2(R)-carboxylic acid

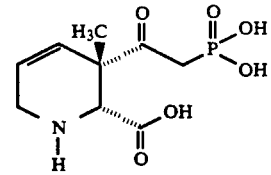

Step a: N-(9-Phenylfluorenyl)-3(R)-methyl-4-piperidene-2(R)-carboxylic acid, tert-butyl ester Dissolve diisopropylamine (0.17 mL, 0.79 mmol) in anhydrous tetrahydrofuran (4.8 mL), cool to 0° C. and place under an inert atmosphere. Add n-butyllithium (0.75 mL of a 1.6M solution in hexane, 1.20 mmol) and cool to −78° C. Add, by dropwise addition, hexamethylphosphoramide (0.22 mL. 1.26 mmol), keeping the temperature below −60° C. Stir at −78° C. for 30 minutes and add, by dropwise addition, a solution of N-(9-phenylfluorenyl)-3-piperidene-2(R)-tert-butyl ester-3-methyl ester (380 mg, 0.79 mmol) in anhydrous tetrahydrofuran (5 mL). Warm to −50° C. to −45° C. and stir for 1 hour, maintaining a temperature of −50° C. to −38° C. Cool to −78° C. and transfer via cannula to a −78° C. solution of iodomethane (0.21 mL, 3.37 mmol). Stir at −78° C. overnight and add add methanol (2 mL) and phosphoric acid (15 mL of a 0.5M solution). Extract into ether ether (3×10 mL), dry ($Na_2SO_4/MgSO_4$) and evaporate the solvent in vacuo to give a dark yellow oil. Purify by silica gel chromatography (25/75 ethyl acetate/hexane) to give the title compound (170 mg, 43%).

$^1$H NMR (300 MHz, $CDCl_3$) ppm 7.15–7.8 (m, 13), 6.12 (m, 1), 5.80 (m, 1), 3.84 (m, 1), 3.68 (s, 1), 3.52 (s, 3), 2.69 (s, 3), 1.25 (m, 1), 0.92 (s, 9).

Step b:
N-(9-Phenylfluorenyl)-3(S)-[(diethoxyphosphinyl)acetyl]-3(R)-methyl-4-piperidene-2(R)-carboxylic acid, tert-butyl ester Dissolve diethyl methylphosponate (1.14 g, 7.5 mmol) in anhydrous tetrahydrofuran (10 mL), cool to −78° C. and place under an inert atmosphere. Add n-butyllithium (4.68 mL of a 1.6M solution in hexane, 7.5 mmol) and stir for 20 minutes. Add, by dropwise addition, a solution of N-(9-Phenylfluorenyl)-3(R)-methyl-4-piperidene-2(R)-carboxylic acid, tert-butyl ester (560 mg, 1.1 mmol) in anhydrous tetrahydrofuran (10 mL). Stir for 4 hours at −48° C. and add acetic acid (2 mL). Warm to room temperature, evaporate to a residue and purify by silica gel chromatography (ethyl acetate) to give the title compound.

Step c:
3(S)-(Phosphonoacetyl]-3(R)-methyl-4-piperidene-2(R)-carboxylic acid Dissolve N-(9-phenylfluorenyl)-3(S)-[(diethoxyphosphinyl)acetyl]-3(R)-methyl-4-piperidene-2(R)-carboxylic acid, tert-butyl ester (0.35 g) in acetonitrile and cool to 0° C. Stir vigorously and add, by dropwise addition, a solution of trifluoroacetic acid (20 mL) in water (2 mL). Stir for 15 minutes, warm to room temperature and stir for 3 hours. Evaporate to a solid residue, take up in water (100 mL) and wash with toluene (100 mL). Freeze dry the aqueous phase to give a residue. Take up the residue in acetonitrile (10 mL) and methylene chloride (10 mL). Pass a gentle stream of nitrogen through the solution and add trimethylsilyliodide (2 mL). Stir for 6 hours, quench with water and wash with toluene (5×100 mL). Freeze dry the aqueous phase and dissolve the resulting residue in methanol (5 mL) and isopropanol (2.5 mL). Add propylene oxide (2.0 mL) and stir for 2 hours. Filter to give the title compound.

The following compounds can be prepared in a similar fashion to that described above in Examples 13 and 14:

3(S)-(Phosphonoacetyl]-3(R)-methyl-5-methyl-4-piperidene-2(R)-carboxylic acid;

3(S)-(Phosphonoacetyl]-3(R)-methyl-5-benzyl-4-piperidene-2(R)-carboxylic acid.

The pyrrolidine compounds of Formula I wherein $R_5$ is hydrogen can be prepared by techniques and procedures well known and appreciated by one of ordinary skill in the art. A general synthetic procedure for preparing these compounds is set forth in Scheme K. In Scheme K all substituents unless otherwise indicated are as previously defined.

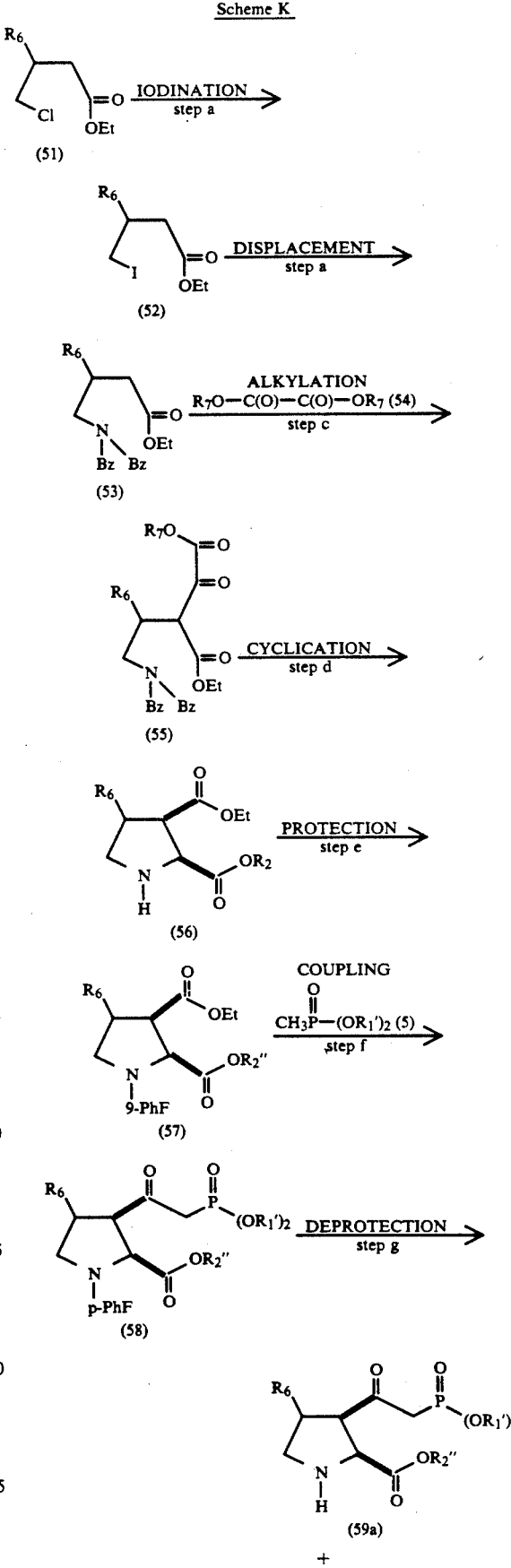

-continued
Scheme K

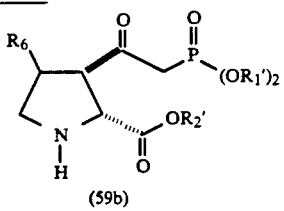

(59b)

Bz = CH₂—C₆H₅

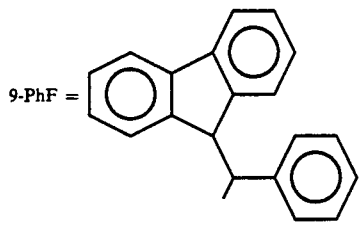

9-PhF =

$R_1' = C_1-C_4$ alkyl or $CF_3$
$R_2'' = CH_2C_6H_5$ or $C_1-C_4$ alkyl
$R_7 = $ Et or t-Bu Scheme K provides a general synthetic procedure for preparing the pyrrolidine compounds of Formula I wherein $R_5$ is hydrogen.

In step a, the 4-chloro functionality of the appropriate ethyl 4-chlorobutyrate of structure (51) is exchanged to give the corresponding ethyl 3-iodobutyrate of structure (52) as described previously in Scheme F, step e.

In step b, the 4-iodo functionality of the appropriate ethyl 4-iodobutyrate of structure (52) is displaced with dibenzylamine to give the corresponding 4-dibenzylaminobutyric acid, ethyl ester of structure (53).

For example, the appropriate ethyl 4-iodobutyrate of structure (52) is contacted with a molar equivalent of benzylamine and a molar equivalent of a suitable base, such as potassium carbonate. The reactants are typically contacted in a suitable organic solvent such as ethanol. The reactants are typically stirred together at room temperature for a period of time ranging from 2-24 hours. The 4-dibenzylaminobutyric acid, ethyl ester of structure (53) is recovered from the reaction zone by evaporation of the solvent. It may be purified by silica gel chromatography.

In step c, the appropriate 4-dibenzylaminobutyric acid, ethyl ester of structure (53) is alkylated with an appropriate dialkyl oxylate of structure (54) to give the corresponding 4-dibenzylamino-2-alkyloxylyl-butyric acid, ethyl ester of structure (55).

For example, the appropriate 4-dibenzylaminobutyric acid, ethyl ester of structure (53) is contacted with a molar equivalent of the appropriate dialkyl oxylate of structure (54) and a molar equivalent of a base such as potassium carbonate. The reactants are typically contacted in a suitable organic solvent mixture such as ethanol/benzene. The reactants are typically stirred together at a temperature range of from room temperature to reflux for a period of time of from 2-24 hours. The 4-dibenzylamino-2-alkyloxylyl-butyric acid, ethyl ester of structure (55) is recovered from the reaction zone by acidification and evaporation of the solvent. It may be purified by silica gel chromatography.

In step d, the appropriate 4-dibenzylamino-2-alkyloxylyl-butyric acid, ethyl ester of structure (55) is cyclyzed to give the corresponding d,l-cis-pyrrolidine-2-alkylcarboxylate-3-ethylcarboxylate of structure (56).

For example, the appropriate 4-dibenzylamino-2-alkyloxylyl-butyric acid, ethyl ester of structure (55) is contacted with a catalytic amount of a hydrogenation catyalyst such as palladium hydroxide. The reactants are typically contacted in a suitable organic solvent such as ethanol. The reactants are typically shaken at room temperature in the presence of hydrogen at a pressure of 30-50 psi for a period of time ranging from 2-16 hours. The d,l-cis-pyrrolidine-2-alkylcarboxylate-3-ethylcarboxylate of structure (56) is recovered from the reaction zone by filtration and evaporation of the solvent. It may be purified by silica gel chromatography.

In step e, the appropriate d,l-cis-pyrrolidine-2-alkylcarboxylate-3-ethylcarboxylate of structure (56) is protected to give the corresponding d,l-cis-N-(9-phenylfluorenyl)pyrrolidine-2-alkylcarboxylate-3-ethylcarboxylate of structure (57) as described previously in Scheme A, step b.

In step f, the appropriate d,l-cis-N-(9-phenylfluorenyl)pyrrolidine-2-alkylcarboxylate-3-ethylcarboxylate of structure (57) is coupled with the appropriate phosphonate ester of structure (5) to give the corresponding d,l-cis-N-(9-phenylfluorenyl)-3-[(dialkoxyphosphinyl)acetyl]pyrrolidine-2-carboxylic acid, ester of structure (58) as described previously in Scheme A, step d.

In step g, the appropriate d,l-cis-N-(9-phenylfluorenyl)-3-[(dialkoxyphosphinyl)acetyl]pyrrolidine-2-carboxylic acid, ester of structure (58) is deprotected to give the corresponding d,l-cis-3-[(dialkoxyphosphinyl)acetyl]pyrrolidine-2-carboxylic acid, ester of structure (59a) and the d,l-trans-3-[(dialkoxyphosphinyl)acetyl]pyrrolidine-2-carboxylic acid, ester of structure (59b) as described previously in Scheme A, step f.

The appropriate d,l-cis-3-[(dialkoxyphosphinyl)acetyl]pyrrolidine-2-carboxylic acid, ester of structure (59a) and the d,l-trans-3[(dialkoxyphosphinyl)acetyl]pyrrolidine-2-carboxylic acid, ester of structure (59b) can be separated into their diastereomeric pairs as shown previously in Scheme B.

Alternatively the enantiomericaly pure 3(S)-[(dialkoxyphosphinyl)acetyl]pyrrolidine-2(R)-carboxylic acid, ester and enantiomericaly pure 3(R)-[(dialkoxyphosphinyl)acetyl]pyrrolidine-2(S)-carboxylic acid, ester can be prepared as set forth in Scheme K by subjecting the appropriate d,l-cis-3-[(dialkoxyphosphinyl)acetyl]pyrrolidine-2-carboxylic acid, ester of structure (59a) and the d,l-trans-3-[(dialkoxyphosphinyl)acetyl]pyrrolidine-2-carboxylic acid, ester of structure (59b) to an enzymatic hydrolysis as described previously in Scheme D, step c and Scheme E, optional step d.

In addition, the enantiomericaly pure 3(S)-[(dialkoxyphosphinyl)acetyl]pyrrolidine-2(R)-carboxylic acid, ester and enantiomericaly pure 3(R)-[(dialkoxyphosphinyl)acetyl]pyrrolidine-2(S)-carboxylic acid, ester can be prepared as set forth in Scheme K by subjecting the appropriate d,l-cis-3-[(dialkoxyphosphinyl)acetyl]pyrrolidine-2-carboxylic acid, ester of structure (59a) to an enzymatic hydrolysis as described previously in Scheme D, step c and Scheme E, optional step d.

Similarly, the enantiomericaly pure 3(S)-[(dialkoxyphosphinyl)acetyl]pyrrolidine-2(S)-carboxylic acid, ester and enantiomericaly pure 3(R)-[(dialkoxyphosphinyl)acetyl]pyrrolidine-2(R)-carboxylic acid, ester can be prepared as set forth in Scheme K by subjecting the appropriate d,l-trans-3-[(dialkoxyphosphinyl)acetyl]pyrrolidine-2-carboxylic acid, ester of structure (59b) to an enzymatic hydrolysis as described previously in Scheme D, step c and Scheme E, optional step d.

The appropriate 3-[(dialkoxyphosphinyl)acetyl]pyrrolidine-2-carboxylic acid, ester of Formula I described above in Scheme K can be further functionalized as described previously in Scheme A, steps $g_1$-i.

The appropriate 3-[(functionalized phosphinyl)acetyl]pyrrolidine-2-carboxylic acid derivatives of Formula I prepared as described above in Scheme K may also be further functionalized into the corresponding 3-[1-imino-2-phosponoethyl]pyrrolidine-2-carboxylic acid derivatives of Formula I as described previously in Scheme C, step a.

Starting materials for use in Scheme K are readily available to one of ordinary skill in the art.

The following examples present typical syntheses as described in Scheme K. These examples are intended to be illustrative only and are not intended to limit the scope of the present invention in any way.

EXAMPLE 15 d,l-cis-3-(Phosphonoacetyl)pyrrolidine-4-methyl-2-carboxylic acid and
d,l-trans-3-(Phosphonoacetyl)pyrrolidine-4-methyl-2-carboxylic acid

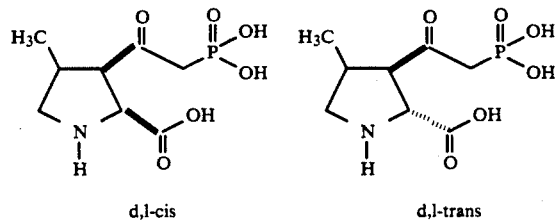

d,l-cis          d,l-trans

Step a: Ethyl 4-iodo-3-methylbutyrate

Mix ethyl 4-chloro-3-methylbutyrate (80 g), acetone (400 mL) and sodium iodide (100 g). Reflux for 8 hours, cool and add methylene chloride (400 mL). Filter and evaporate the filtrate to a residue. Partition the residue between methylene chloride (200 mL) and water (200 mL). Separate the organic phase, dry ($MgSO_4$) and evaporate to an oil. Purify by distillation to give the title compound.

Step b: 4-Dibenzylamino-3-methylbutyric acid, ethyl ester

Mix ethyl 4-iodo-3-methylbutyrate (4.61 g, 0.18 mol), dibenzylamine (35.5 g, 0.18 mol), potassium carbonate (24.9 g, 0.18 mol) and ethanol (114 mL dried over 4A molecular sieves). Reflux for 24 hours then stir at room temperature for 48 hours. Add methylene chloride (100 mL) and filter. Evaporate the filtrate to a residue and purify by silica gel chromatography to give the title compound.

Step c: 4-Dibenzylamino-3-methyl-2-tert-butyloxylyl-butyric acid, ethyl ester Mix 4-dibenzylamino-3-methylbutyric acid, ethyl ester (20.5 g, 63 mmol), tert-butyl methyl oxylate (10 g, 63 mmol), potassium carbonate (9.3 g), ethanol (5 mL) and benzene (150 mL). Stir overnight at room temperature under a nitrogen atmosphere. Add ethanol (10 mL) and stir for an additional hour. Quench with acetic acid until the dark color clears to a light yellow, filter through celite and evaporate the filtrate to an oil. Purify by silica gel chromatography to give the title compound.

Step d: d,l-cis-Pyrrolidine-4-methyl-2-tert-butylcarboxylate-3-ethylcarboxylate Mix 4-dibenzylamino-3-methyl-2-tert-butyloxylyl-butyric acid, ethyl ester (10 g), 20% palladium hydroxide on carbon (1 g) and ethanol. Place on a Paar Hydrogenation apparatus and hydrogenate at 30 psi for 3 hours. Filter and evaporate to an oil. Purify by silica gel chromatography to give the title compound.

Step e: d,l-cis-N-(9-Phenylfluorenyl)pyrrolidine-4-methyl-2-tert-butylcarboxylate-3-ethylcarboxylate Mix d,l-cis-pyrrolidine-4-methyl-2-tert-butylcarboxylate-3-ethylcarboxylate (5 g), 9-phenylfluorenyl bromide (8.39 g, 26 mmol), lead nitrate (3.9 g, 24 mmol), diisopropylethylamine (5 mL, 28 mmol) and acetonitrile (100 mL). Stir at room temperature for 4 hours and add methylene chloride (200 ml). Fitler through silica gel and evaporate the filtrate to an oil. Purify by silica gel chromatography to give the title compound.

Step f: d,l-cis-N-(9-Phenylfluorenyl)-3-[(diethoxyphosphinyl)acetyl]pyrrolidine-4-methyl-2-carboxylic acid, tert-butyl ester Dissolve diethyl methylphosphonate (9.25 g, 60 mmol) in anhydrous tetrahydrofuran (50 mL), cool to −78° C. and place under a nitrogen atmosphere. Add n-butyllithium (37.5 mL of a 1.6M solution in hexane, 60 mmol) and stir for ½ hour. Add a solution of d,l-cis-N-(9-phenylfluorenyl)pyrrolidine-4-methyl-2-tert-butylcarboxylate-3-ethylcarboxylate (10.2 g, 20 mmol) in tetrahydrofuran (50 mL) and stir at −78° C. for 1 hour. Quench with acetic acid and pour into saturated sodium chloride (100 mL). Extract with ethyl acetate (2×100 mL) and dry. Purify by silica gel chromatography to give the title compound.

Step g: d,l-cis-3-(Phosphonoacetyl)pyrrolidine-4-methyl-2-carboxylic acid and
d,l-trans-3-(Phosphonoacetyl)pyrrolidine-4-methyl-2-carboxylic acid Stir d,l-cis-N-(9-phenylfluorenyl)-3-[(diethoxyphosphinyl)acetyl]pyrrolidine-4-methyl-2-carboxylic acid, tert-butyl ester (3 g) with trifluoroacetic acid (30 mL) and water (1 mL). Blow to a residue with a stream of nitrogen, take up the residue in water (120 mL) and wash with ethyl acetate (75 mL). Freeze dry the aqueous phase to give a yellow oil. Dissolve the yellow oil in acetonitrile (20 mL) and methylene chloride (20 mL). Add trimethylsilyl iodide (3.5 mL, 24 mmol) and stir for 5 hours. Pour into water (250 mL) and wash with toluene (3×250 mL). Freeze dry the aqueous phase to give a solid residue. Take up the solid residue in methanol (10 mL) and isopropanol (5 mL). Add propylene oxide (2 mL) and stir for 1 hour. Filter and dry to give the title compounds. Separate by High Performance Liquid Chromatography on a P/10 SAX M/20-24 (Whatman) Column with 0.025M hydrochloric acid/acetonitrile to give the separate title compounds.

EXAMPLE 16 d,l-cis-3-(Phosphonoacetyl]pyrrolidine-2-carboxylic acid and
d,l-trans-3-(Phosphonoacetyl]pyrrolidine-2-carboxylic acid

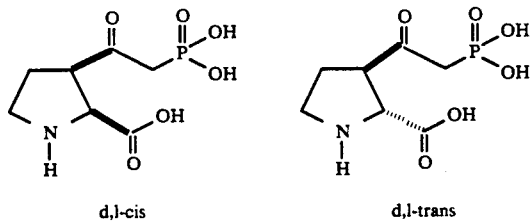

Step a: Ethyl 4-iodobutyrate

Mix ethyl 4-chlorobutyrate (80 g), acetone (400 mL) and sodium iodide (100 g). Reflux for 8 hours, cool and add methylene chloride (400 mL). Filter and evaporate the filtrate to a residue. Partition the residue between methylene chloride (200 mL) and water (200 mL). Separate the organic phase, dry (MgSO$_4$) and evaporate to an oil. Purify by distillation to give the title compound (89 g); bp 64° C.@0.5 mm Hg.

Step b: 4-Dibenzylaminobutyric acid, ethyl ester

Mix ethyl 4-iodobutyrate (43.5 g, 0.18 mol), dibenzylamine (35.5 g, 0.18 mol), potassium carbonate (24.9 g, 0.18 mol) and ethanol (114 mL dried over 4A molecular sieves). Reflux for 24 hours then stir at room temperature for 48 hours. Add methylene chloride (100 mL) and filter. Evaporate the filtrate to a residue and purify by silica gel chromatography (methylene chloride) to give the title compound (47 g).

$^1$H NMR (90 MHz, CDCl$_3$) ppm 3.95 (q, 2), 4.35 (s, 4), 2.40 (t, 2), 2.25 (t, 2), 1.75 (q, 2), 1.1 (t, 3).

Step c: 4-Dibenzylamino-2-tert-butyloxylyl-butyric acid, ethyl ester

Mix 4-dibenzylaminobutyric acid, ethyl ester (19.5 g, 63 mmol), tert-butyl methyl oxylate (10 g, 63 mmol), potassium carbonate (9.3 g), ethanol (5 mL) and benzene (150 mL). Stir overnight at room temperature under a nitrogen atmosphere. Add ethanol (10 mL) and stir for an additional hour. Quench with acetic acid until the dark color clears to a light yellow, filter through celite and evaporate the filtrate to an oil. Purify by silica gel chromatography (ethyl acetate/hexane) to give the title compound.

Step d: d,l-cis-Pyrrolidine-2-tert-butylcarboxylate-3-ethylcarboxylate

Mix 4-dibenzylamino-2-tert-butyloxylyl-butyric acid, ethyl ester (10 g), 20% palladium hydroxide on carbon (1 g) and ethanol. Place on a Paar Hydrogenation apparatus and hydrogenate at 30 psi for 3 hours. Filter and evaporate to an oil. Purify by silica gel chromatography (90:10 ethyl acetate/hexane) to give the title compound (5.2 g).

Step e: d,l-cis-N-(9-Phenylfluorenyl)pyrrolidine-2-tert-butylcarboxylate-3-ethylcarboxylate Mix d,l-cis-pyrrolidine-2-tert-butylcarboxylate-3-ethylcarboxylate (5 g), 9-phenylfluorenyl bromide (8.39 g, 26 mmol), lead nitrate (3.9 g, 24 mmol), diisopropylethylamine (5 mL, 28 mmol) and acetonitrile (100 mL). Stir at room temperature for 4 hours and add methylene chloride (200 ml). Fitler through silica gel and evaporate the filtrate to an oil. Purify by silica gel chromatography (70% ethyl acetate/hexane) to give the title compound (9.5 g).

Step f: d,l-cis-N-(9-Phenylfluorenyl)-3-[(diethoxyphosphinyl)acetyl]pyrrolidine-2-carboxylic acid, tert-butyl ester Dissolve diethyl methylphosphonate (9.25 g, 60 mmol) in anhydrous tetrahydrofuran (50 mL), cool to −78° C. and place under a nitrogen atmosphere. Add n-butyllithium (37.5 mL of a 1.6M solution in hexane, 60 mmol) and stir for ½ hour. Add a solution of d,l-cis-N-(9-phenylfluorenyl)pyrrolidine-2-tert-butylcarboxylate-3-ethylcarboxylate (9.5 g, 20 mmol) in tetrahydrofuran (50 mL) and stir at −78° C. for 1 hour. Quench with acetic acid and pour into saturated sodium chloride (100 mL). Extract with ethyl acetate (2×100 mL) and dry. Purify by silica gel chromatography (70:30 ethyl acetate/hexane) to give the title compound (3.2 g).

$^1$H NMR (300 MHz, CDCl$_3$) ppm 7.2–7.75 (m, 13), 4.05 (m, 4), 3.64 (d, 1), 3.32 (t, 1), 3.15 (m, 2), 2.92 (dd, 1), 2.79 (m, 1), 2.35 (m, 1), 1.8 (m, 1), 1.29 (s, 9), 1.22 (m, 6).

Step g: d,l-cis-3-(Phosphonoacetyl]pyrrolidine-2-carboxylic acid and
d,l-trans-3-(Phosphonoacetyl]pyrrolidine-2-carboxylic acid Stir d,l-cis-N-(9-phenylfluorenyl)-3-[(diethoxyphosphinyl)acetyl]pyrrolidine-2-carboxylic acid, tert-butyl ester (3 g) with trifluoroacetic acid (30 mL) and water (1 mL). Blow to a residue with a stream of nitrogen, take up the residue in water (120 mL) and wash with ethyl acetate (75 mL). Freeze dry the aqueous phase to give a yellow oil. Dissolve the yellow oil in acetonitrile (20 mL) and methylene chloride (20 mL). Add trimethylsilyl iodide (3.5 mL, 24 mmol) and stir for 5 hours. Pour into water (250 mL) and wash with toluene (3×250 mL). Freeze dry the aqueous phase to give a solid residue. Take up the solid residue in methanol (10 mL) and isopropanol (5 mL). Add propylene oxide (2 mL) and stir for 1 hour. Filter and dry to give the title compounds (1.0 g). Separate by High Performance Liquid Chromatography on a P/10 SAX M/20-24 (Whatman) Column with 0.025M hydrochloric acid/acetonitrile to give the separate title compounds with the trans eluting first.

trans $^1$H NMR (300 MHz, D$_2$O) ppm 4.8 (d, 1), 3.95 (m, 1), 3.55 (m, 1), 3.2–3.5 (m, 3), 2.51 (m, 1), 2.28 (m, 1).

cis $^1$H NMR (300 MHz, D$_2$O) ppm 4.59 (d, 1), 4.19 (m, 1), 3.51 (m, 1), 3.2–3.5 (m, 3), 2.49 (m, 1), 2.41 (m, 1).

The pyrrolidine compounds of Formula I wherein R$_5$ is linear C$_1$-C$_4$ alkyl or alkylphenyl can be prepared by techniques and procedures well known and appreciated by one of ordinary skill in the art. A general synthetic procedure for preparing these compounds is set forth in Scheme L. In Scheme L all substituents unless otherwise indicated are as previously defined.

Scheme L

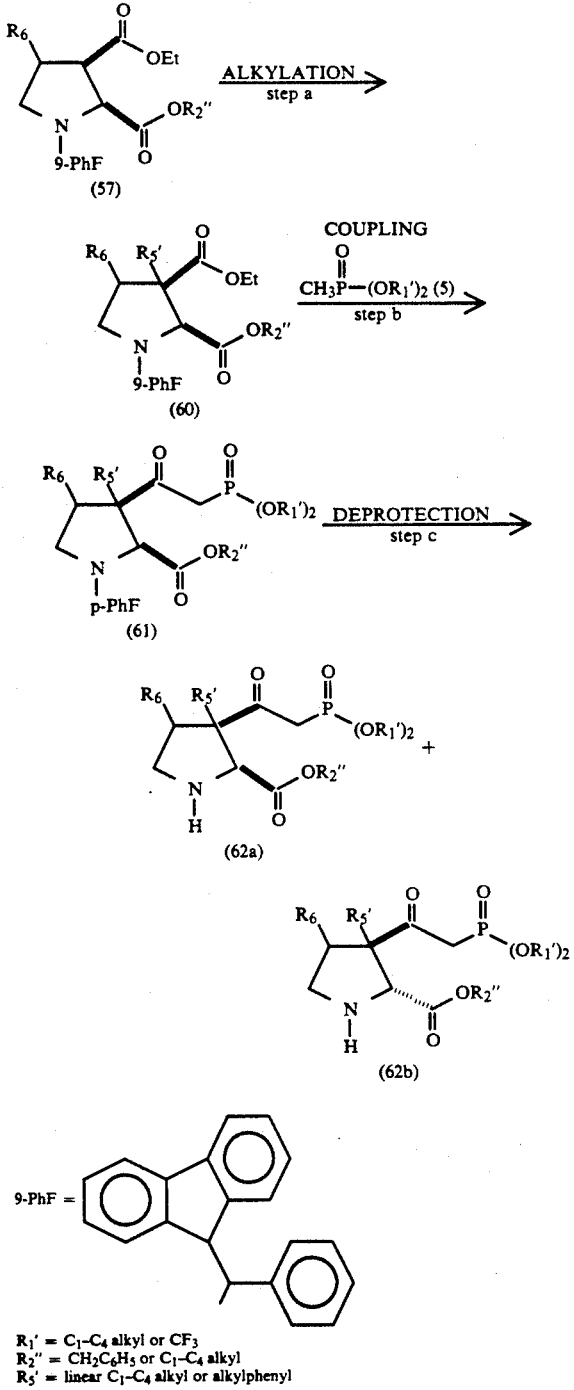

$R_1'$ = $C_1$-$C_4$ alkyl or $CF_3$
$R_2''$ = $CH_2C_6H_5$ or $C_1$-$C_4$ alkyl
$R_5'$ = linear $C_1$-$C_4$ alkyl or alkylphenyl Scheme L provides a general synthetic procedure for preparing the pyrrolidine compounds of Formula I wherein $R_5$ is linear $C_1$-$C_4$ alkyl or alkylphenyl.

In step a, the appropriate d,l-cis-N-(9-phenylfluorenyl)pyrrolidine-2-alkylcarboxylate-3-ethylcarboxylate of structure (57) is alkylated with an appropriate alkylating agent of the formula $R_5'$-Hal to give the corresponding d,l-cis-N-(9-phenylfluorenyl)pyrrolidine-2-alkylcarboxylate-3-alkyl-3-ethylcarboxylate of structure (60).

For example, the appropriate d,l-cis-N-(9-phenylfluorenyl)pyrrolidine-2-alkylcarboxylate-3-ethylcarboxylate of structure (57) is contacted with a molar equivalent of a suitable non-nucleophilic base, such as lithium diisopropylamide. The reactants are typically contacted in a suitable organic solvent such as tetrahydrofuran. The reactants are typically stirred together for a period of time ranging from 2-24 hours and at a temperature range of from $-78°$ C. to $0°$ C. The d,l-cis-N-(9-phenylfluorenyl)pyrrolidine-2-alkylcarboxylate-3-alkyl-3-ethylcarboxylate of structure (60) is recovered from the reaction zone by a low-temperature quench into the appropriate alkylating agent of the formula $R_5'$-Hal, followed by extraction by methods known in the art. It may be purified by silica gel chromatography.

In step b, the appropriate d,l-cis-N-(9-phenylfluorenyl)pyrrolidine-2-alkylcarboxylate-3-alkyl-3-ethylcarboxylate of structure (60) is coupled with the appropriate phosphonate ester of structure (5) to give the corresponding d,l-cis-N-(9-phenylfluorenyl)-3-[(dialkoxyphosphinyl)acetyl]pyrrolidine-3-alkyl-2-carboxylic acid, ester of structure (61) as described previously in Scheme A, step d.

In step c, the appropriate d,l-cis-N-(9-phenylfluorenyl)-3-[(dialkoxyphosphinyl)acetyl]pyrrolidine-3-alkyl-2-carboxylic acid, ester of structure (61) is deprotected to give the corresponding d,l-cis-3-[(dialkoxyphosphinyl)acetyl]pyrrolidine-3-alkyl-2-carboxylic acid, ester of structure (62a) and d,l-trans-3-[(dialkoxyphosphinyl)acetyl]pyrrolidine-3-alkyl-2-carboxylic acid, ester of structure (62b) as described previously in Scheme A, step f.

The appropriate d,l-cis-3-[(dialkoxyphosphinyl)acetyl]pyrrolidine-3-alkyl-2-carboxylic acid, ester of structure (62a) and d,l-trans-3-[(dialkoxyphosphinyl)acetyl]pyrrolidine-3-alkyl-2-carboxylic acid, ester of structure (62b) can be separated into their diastereomeric pairs as shown previously in Scheme B.

In addition, the enantiomericaly pure 3(S)-[(dialkoxyphosphinyl)acetyl]pyrrolidine-3-alkyl-2(R)-carboxylic acid, ester and enantiomericaly pure 3(R)-[(dialkoxyphosphinyl)acetyl]pyrrolidine-3-alkyl-2(S)-carboxylic acid, ester can be prepared as set forth in Scheme K by subjecting the appropriate d,l-cis-3-[(dialkoxyphosphinyl)acetyl]pyrrolidine-3-alkyl-2-carboxylic acid, ester of structure (62a) to an enzymatic hydrolysis as described previously in Scheme D, step c and Scheme E, optional step d.

Similarly, the enantiomericaly pure 3(S)-[(dialkoxyphosphinyl)acetyl]pyrrolidine-3-alkyl-2(S)-carboxylic acid, ester and enantiomericaly pure 3(R)-[(dialkoxyphosphinyl)acetyl]pyrrolidine-3-alkyl-2(R)-carboxylic acid, ester can be prepared as set forth in Scheme K by subjecting the appropriate d,l-trans-3-[(dialkoxyphosphinyl)acetyl]pyrrolidine-3-alkyl-2-carboxylic acid, ester of structure (62b) to an enzymatic hydrolysis as described previously in Scheme D, step c and Scheme E, optional step d.

The appropriate 3-[(dialkoxyphosphinyl)acetyl]pyrrolidine-2-carboxylic acid, ester of Formula I described above in Scheme K can be further functionalized as described previously in Scheme A, steps $g_1$-i.

The appropriate d,l-cis-3-[(dialkoxyphosphinyl)acetyl]pyrrolidine-3-alkyl-2-carboxylic acid, ester of structure (62a) and d,l-trans-3-[(dialkoxyphosphinyl)acetylpyrrolidine-3-alkyl-2-carboxylic acid, ester of structure (62b) can be further functionalized as described previously in Scheme A, steps $g_1$-i.

The appropriate 3-[(functionalized phosphinyl)acetyl]pyrrolidine-3-alkyl-2-carboxylic acid derivatives of Formula I prepared as described above in Scheme L may also be further functionalized into the corresponding 3-[1-imino-2-phosponoethyl]pyrrolidine-3-alkyl-2-carboxylic acid derivatives of Formula I as described previously in Scheme C, step a.

Starting materials for use in Scheme L are readily available to one of ordinary skill in the art.

The following examples present typical syntheses as described in Scheme L. These examples are intended to be illustrative only and are not intended to limit the scope of the present invention in any way.

EXAMPLE 17 d,l-cis-3-(Phosphonoacetyl)pyrrolidine-3-methyl-2-carboxylic acid and
d,l-trans-3-(Phosphonoacetyl)pyrrolidine-3-methyl-2-carboxylic acid

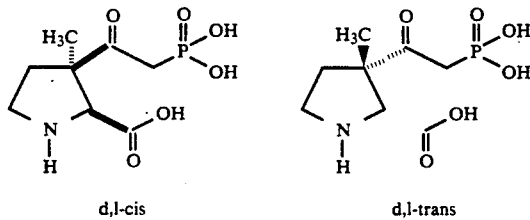

d,l-cis      d,l-trans

Step a:
d,l-cis-N-(9-Phenylfluorenyl)pyrrolidine-2-tert-butylcarboxylate-3-methyl-3-ethylcarboxylate Dissolve diisopropylamine (0.6 mL, 4.3 mmol) in tetrahydrofuran (10 mL) and cool to 0° C. Add, by dropwise addition, n-butyllithium (2.7 mL of a 1.6M solution, 4.3 mmol). Stir for ½ hour, cool to −78° C. and add, by dropwise addition, a solution of d,l-cis-N-(9-phenylfluorenyl)pyrrolidine-2-tert-butylcarboxylate-3-ethylcarboxylate (795 mg, 1.6 mmol) in tetrahydrofuran (10 mL). Stir for 1 hour at −78° C. and then for 3 hours at −30° C. Transfer rapidly, via water heated cannula, to a −78° C. solution of iodomethane (426 mg, 3 mmol) in tetrahydrofuran (10 mL). Allow to warm to room temperature overnight. Add ethyl acetate and wash with brine. Evaporate to a residue and purify by silica gel chromatography to give the title compound.

Step b:
d,l-cis-N-(9-Phenylfluorenyl)-3-[(diethoxyphosphinyl)acetyl]pyrrolidine-3-methyl-2-carboxylic acid, tert-butyl ester Dissolve diethyl methylphosphonate (9.25 g, 60 mmol) in anhydrous tetrahydrofuran (50 mL), cool to −78° C. and place under a nitrogen atmosphere. Add n-butyllithium (37.5 mL of a 1.6M solution in hexane, 60 mmol) and stir for ½ hour. Add a solution of d,l-cis-N-(9-phenylfluorenyl)pyrrolidine-3-methyl-2-tert-butylcarboxylate-3-ethylcarboxylate (10.2 g, 20 mmol) in tetrahydrofuran (50 mL) and stir at −78° C. for 1 hour. Quench with acetic acid and pour into saturated sodium chloride (100 mL). Extract with ethyl acetate (2×100 mL) and dry. Purify by silica gel chromatography (70:30 ethyl acetate/hexane) to give the title compound.

Step c:
d,l-cis-3-(Phosphonoacetyl)pyrrolidine-3-methyl-2-carboxylic acid and
d,l-trans-3-(Phosphonoacetyl)pyrrolidine-2-carboxylic acid Stir d,l-cis-N-(9-phenylfluorenyl)-3-[(diethoxyphosphinyl)acetyl]pyrrolidine-3-methyl-2-carboxylic acid, tert-butyl ester (3 g) with trifluoroacetic acid (30 mL) and water (1 mL). Blow to a residue with a stream of nitrogen, take up the residue in water (120 mL) and wash with ethyl acetate (75 mL). Freeze dry the aqueous phase to give a yellow oil. Dissolve the yellow oil in acetonitrile (20 mL) and methylene chloride (20 mL). Add trimethylsilyl iodide (3.5 mL, 24 mmol) and stir for 5 hours. Pour into water (250 mL) and wash with toluene (3×250 mL). Freeze dry the aqueous phase to give a solid residue. Take up the solid residue in methanol (10 mL) and isopropanol (5 mL). Add propylene oxide (2 mL) and stir for 1 hour. Filter and dry to give the title compounds (1.0 g). Separate by High Performance Liquid Chromatography on a P/10 SAX M/20-24 (Whatman) Column with 0.025M hydrochloric acid/acetonitrile to give the separate title compounds.

The compounds of Formula I are excitatory amino acid antagonists. They antagonize the effects which excitatory amino acids have upon the NMDA receptor complex. They preferentially bind to the glutamate binding site located on the NMDA receptor complex. They are useful in the treatment of a number of disease states.

The compounds exhibit anti-convulsant properties and are useful in the treatment of epilepsy. They are useful in the treatment of grand mal seizures, petit mal seizures, psychomotor seizures, and autonomic seizures. One method of demonstrating their anti-epileptic properties is by the compounds ability to inhibit audiogenic convulsions in DBA/2 mice. This test can be conducted in the following manner.

Typically one group of from 6–8 male DBA/2J audiogenic susceptible mice are administered from about 0.01 µg to about 100 µg of the test compound. The test compound is administered intracerebrally into the lateral ventricle of the brain. A second group of mice are administered an equal volume of a saline control by the same route. Five minutes later the mice are placed individually in glass jars and are exposed to a sound stimulus of 110 decibels for 30 seconds. Each mouse is observed during the sound exposure for signs of seizure activity. The control group will have a statistically higher incidence of seizures than the group which receives the test compound.

Another method for demonstrating the anti-epileptic properties of these compounds is by their ability to inhibit the seizures that are caused by the administration of quinolinic acid. This test can be conducted in the following manner.

One group containing ten mice are administered 0.01–100 ug of test compound intracerebroventricularly in a volume of 5 microliter of saline. A second control group containing an equal number of mice are administered an equal volume of saline as a control. Approximately 5 minutes later, both groups are administered 7.7 micrograms of quinolinic acid intracerebroventricularly in a volume of 5 microliters of saline. The animals are observed for 15 minutes thereafter for signs of clonic seizures. The control group will have a statistically higher rate of clonic seizures than will the test group.

The compounds of Formula I are useful for preventing or minimizing the damage which nervous tissues contained within the CNS suffer upon exposure to either ischemic, hypoxic, or hypoglycemic conditions. Representative examples of such ischemic, hypoxic, or hypoglycemic conditions include strokes or cerebrovascular accidents, carbon monoxide poisoning, hyperinsulinemia, cardiac arrest, drownings, physical trauma, suffocation, and neonatal anoxic trauma. The compounds should be administered to the patient within 24 hours of the onset of the hypoxic, ischemic, or hypoglycemic condition in order for the compounds to effectively minimize the CNS damage which the patient will experience.

The compounds are also useful in the treatment of neurodegenerative diseases such as Huntington's disease, Alzheimer's disease, senile dementia, glutaric acidaemia type I, multi-infarct dementia, Parkinson's disease and neuronal damage associated with uncontrolled seizures. The administration of these compounds to a patient experiencing such a condition will serve to either prevent the patient from experiencing further neurodegeneration or it will decrease the rate at which the neurodegeneration occurs.

As is apparent to those skilled in the art, the compounds will not correct any CNS damage that has already occurred as the result of either disease or a lack of oxygen or sugar. As used in this application, the term "treat" refers to the ability of the compounds to prevent further damage or delay the rate at which any further damage occurs.

The compounds exhibit an anxiolytic effect and are thus useful in the treatment of anxiety. These anxiolytic properties can be demonstrated by their ability to block distress vocalizations in rat pups. This test is based upon the phenomenon that when a rat pup is removed from its litter, it will emit an ultrasonic vocalization. it was discovered that anxiolytic agents block these vocalizations. The testing methods have been described by Gardner, C. R., Distress vocalization in rat pups: a simple screening method for anxiolytic drugs. *J. Pharmacol. Methods*, 14: 181–187 (1985) and Insel et al., Rat pup ultrasonic isolation calls: Possible mediation by the benzodiapine receptor complex, *Pharmacol. Biochem. Behav.*, 24: 1263–1267 (1986). The compounds also exhibit an analgesic effect and are useful in controlling pain. The compounds may also be utilized to prophylacticaly prevent migraines or to terminate a migraine episode.

In order to exhibit any of these therapeutic properties, the compounds need to be administered in a quantity sufficient to inhibit the effect which the excitatory amino acids have upon the NMDA receptor complex. The dosage range at which these compounds exhibit this antagonistic effect can vary widely depending upon the particular disease being treated, the severity of the patient's disease, the patient, the particular compound being administered, the route of administration, and the presence of other underlying disease states within the patient, etc. Typically the compounds exhibit their therapeutic effect at a dosage range of from about 0.01 mg/kg/day to about 500 mg/kg/day for any of the diseases or conditions listed above. Repetitive daily administration may be desirable and will vary according to the conditions outlined above.

The compounds of the present invention may be administered by a variety of routes. They are effective if administered orally. The compounds may also be administered parenterally (i.e. subcutaneously, intravenously, intramuscularly, intraperitoneally, or intrathecally).

Pharmaceutical compositions can be manufactured utilizing techniques known in the art. Typically an antagonistic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

As used in this application:
a) the term patient refers to warm blooded animals such as, for example, guinea pigs, mice, rats, cats, rabbits, dogs, monkeys, chimpanzees, and humans;
b) the term treat refers to the ability of the compounds to either relieve, alleviate, prevent or slow the progression of the patient's disease;
c) the term neurodegeneration refers to a progressive death and disappearance of a population of nerve cells occurring in a manner characteristic of a particular disease state and leading to brain damage.

The compounds may also be admixed with any inert carrier and utilized in laboratory assays in order to determine the concentration of the compounds within the serum, urine, etc., of the patient as is known in the art.

Neurodegenerative diseases are typically associated with a loss of NMDA receptors. Thus, the compounds of Formula I may be utilized in diagnostic procedures to aid physicians with the diagnosis of neurodegenerative diseases. The compounds may be labeled with isotopic agents by techniques known in the art and utilized as imaging agents. They may then be administered to a patient in order to determine whether the patient is exhibiting a decreased number of NMDA receptors and the rate at which that loss is occurring.

What is claimed is:
1. A compound of the formula:

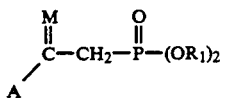

in which $R_1$ is represented by hydrogen, $C_{1-4}$ alkyl or $CF_3$; M is represented by O, N—O—$R_4$, or N—NH—$R_4$ A is represented by one of the following substituents:

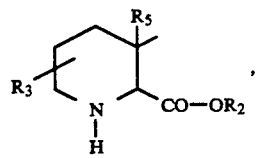

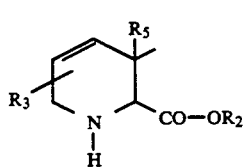

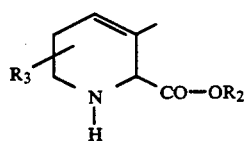

$R_2$ is represented by hydrogen, $C_{1-4}$ alkyl, cyclopentyl, cyclohexyl, trialkylamino, phenyl, substituted phenyl in which the phenyl moiety is substituted with up to 3 substituents with each substituent being independently selected from the group consisting of halogens, $C_1-C_4$ alkyl, $C_1-C_4$ alkoxy, $CF_3$, $OCF_3$, OH, CN, $COOR_6$, and $CONR_6R_7$, phenyl($C_{1-3}$ alkyl) in which the phenyl moiety may be optionally substituted as immediately described above, or trifluoromethyl; $R_3$ is represented by hydrogen, $C_{1-4}$ alkyl, phenyl, phenyl($C_{1-3}$ alkyl), or cyclohexylmethyl; $R_4$ is represented by hydrogen, $C_{1-4}$ alkyl or phenyl($C_{1-3}$ alkyl); $R_5$ is represented by hydrogen, linear $C_{1-4}$ alkyl, or phenyl($C_{1-3}$ alkyl); $R_6$ and $R_7$ are each represented by hydrogen or a $C_1-C_4$ alkyl; trialkylamino is represented by

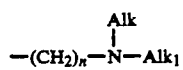

in which n is represented by an integer from 2–4 and Alk and $Alk_1$ are each independently represented by a $C_1-C_4$ alkyl; or a pharmaceutically acceptable salt thereof.

2. A compound according to claim 1 wherein M is O.

3. A compound according to claim 1 wherein M is N—O—$R_4$.

4. A compound according to claim 1 wherein M is

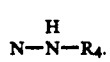

5. A compound according to claim 1 wherein $R_3$ is hydrogen.

6. A compound according to claim 1 in which A is

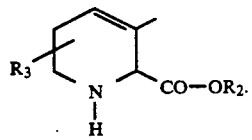

7. A compound according to claim 1 in which A is

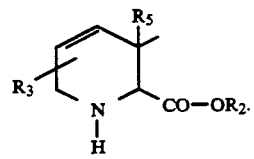

8. A compound according to claim 1 in which A is

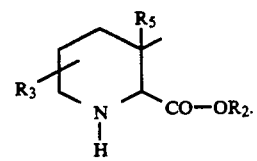

9. A compound according to claim 8 in which $R_5$ and $R_3$ are hydrogen.

10. A method for antagonizing the effects of excitatory amino acids upon the NMDA receptor complex comprising administering to a patient in need thereof, an antagonistic amount of a compound according to claim 1.

11. A method for the treatment of epilepsy comprising administering to a patient in need thereof an antiepileptic amount of a compound according to claim 1.

12. A method for the treatment of neurodegenerative diseases comprising administering to a patient in need thereof an effective amount of a compound according to claim 1.

13. A method for preventing ischemic/hypoxic/hypoglycemic damage to cerebral tissue comprising administering to a patient in need thereof an effective amount of a compound according to claim 1.

14. A method for the treatment of anxiety comprising administering to a patient in need thereof an anxiolytic amount of a compound according to claim 1.

15. A method for producing an analgesic effect comprising administering to a patient in need thereof an analgesic amount of a compound according to claim 1.

16. A pharmaceutical composition comprising a compound according to claim 1 in admixture with a pharmaceutically acceptable carrier.

17. A compound according to claim 1 in which said compound is 3-(phosphonoacetyl)piperidine-2-carboxylic acid.

18. A compound according to claim 1 in which said compound is d,l-trans-3-(phosphonoacetyl)piperidine-2-carboxylic acid.

19. A compound according to claim 1 in which said compound is d,l-cis-3-(phosphonoacetyl)piperidine-2-carboxylic acid.

20. A compound according to claim 1 in which said compound is 3(S)-[(diethoxyphosphinyl)acetyl]piperidine-2(R)-carboxylic acid, methyl ester.

21. A compound according to claim 1 in which said compound is 3(S)-[(diethoxyphosphinyl)acetyl]piperidine-4-methyl-2(R)-carboxylic acid, methyl ester.

22. A compound according to claim 1 in which said compound is 3(R)-[(diethoxyphosphinyl)acetyl]piperidine-4-methyl-2(S)-carboxylic acid, methyl ester.

23. A compound according to claim 1 in which said compound is 3(S)-(phosphonacetyl]piperidine-4-methyl-2(R)-carboxylic acid.

24. A compound according to claim 1 in which said compound is 3(R)-(phosphonacetyl]piperidine-4-methyl-2(S)-carboxylic acid.

25. A compound according to claim 1 in which said compound is 3(S)-[(diethoxyphosphinyl)acetyl]piperidine-5-methyl-2(R)-carboxylic acid, methyl ester.

26. A compound according to claim 1 in which said compound is 3(S)-(phosphonacetyl]piperidine-5-methyl-2(R)-carboxylic acid.

27. A compound according to claim 1 in which said compound is d,l-cis-3-[(diethoxyphosphinyl)acetyl]-piperidine-2-carboxylic acid, methyl ester.

28. A compound according to claim 1 in which said compound is 3(S)-(phosphonacetyl]piperidine-2(R)-carboxylic acid.

29. A compound according to claim 1 in which said compound is 3(S)-(phosphonacetyl]piperidine-5-benzyl-2(R)-carboxylic acid.

30. A compound according to claim 1 in which said compound is 3(R)-(phosphonacetyl]piperidine-2(R)-carboxylic acid, methyl ester.

31. A compound according to claim 1 in which said compound is 3(S)-(phosphonacetyl]piperidine-3(R)-methyl-2(R)-carboxylic acid.

32. A compound according to claim 1 in which said compound is 3-(phosphonacetyl)piperidine-2-carboxylic acid, ethyl ester.

33. A compound according to claim 1 in which said compound is 3(S)-(phosphonacetyl]piperidine-5-benzyl-3(R)-methyl-2(R)-carboxylic acid.

34. A compound according to claim 1 in which said compound is 3-(phosphonacetyl]-3-piperidine-2(R)-carboxylic acid.

35. A compound according to claim 1 in which said compound is 3-(phosphonacetyl]-3-piperidine-5-methyl-2(R)-carboxylic acid.

36. A compound according to claim 1 in which said compound is 3(S)-(phosphonacetyl]-4-piperidine-2(R)-carboxylic acid.

37. A compound according to claim 1 in which said compound is 3(S)-(phosphonacetyl]-3(R)-methyl-4-piperidine-2(R)-carboxylic acid.

38. A compound according to claim 1 in which said compound is 3(S)-(Phosphonoacetyl]-3(R)-methyl-5-methyl-4-piperidine-2(R)-carboxylic acid.

39. A compound according to claim 1 in which said compound is 3(S)-(phosphonacetyl]-3(R)-methyl-5-benzyl-4-piperidine-2(R)-carboxylic acid.

40. A method according to claim 10 utilizing a compound according to claim 17.

41. A method according to claim 10 utilizing a compound according to claim 23.

42. A method according to claim 10 utilizing a compound according to claim 28.

43. A method according to claim 10 utilizing a compound according to claim 8 in which $R_5$ is hydrogen.

44. A compound according to claim 8 in which $R_5$ is hydrogen.

45. A compound according to claim 1 in which said compound is 3-[1-[(Phenylmethoxy)imino]-2-phosphonoethyl]piperidine-2-carboxylic acid.

46. A compound according to claim 1 in which said compound is 3-[(1-Methoxyimino)-2-phosphoneoethyl]-piperidine-5-methyl-2-carboxylic acid.

* * * * *